United States Patent [19]

Sohda et al.

[11] Patent Number: 5,591,862

[45] Date of Patent: Jan. 7, 1997

[54] TETRAZOLE DERIVATIVES, THEIR PRODUCTION AND USE

[75] Inventors: Takashi Sohda, Takatsuki; Hitoshi Ikeda, Higashiosaka; Yu Momose, Takarazuka, all of Japan

[73] Assignee: Takeda Chemical Industries, Ltd., Osaka, Japan

[21] Appl. No.: 257,056

[22] Filed: Jun. 8, 1994

[30] Foreign Application Priority Data

Jun. 11, 1993 [JP] Japan ................ 5-140906

[51] Int. Cl.$^6$ ............ C07D 413/12; C07D 403/14; C07D 401/14; C07D 417/14; A61K 31/425; A61K 31/42; A61K 31/415; A61K 31/44; A61K 31/505

[52] U.S. Cl. ............ 548/235; 548/128; 548/186; 548/251; 548/252; 546/268.4; 546/269.7; 546/256; 546/193; 546/210; 546/271.4; 546/275.1; 546/272.4; 546/270.7; 544/132; 544/333; 514/236.8; 514/256; 514/340; 514/342; 514/362; 514/374; 514/381; 514/382

[58] Field of Search ................ 548/235, 128, 548/186, 251, 252; 546/276, 277; 514/236.8, 256, 340, 342, 362, 374, 381, 382; 544/132, 333

[56] References Cited

U.S. PATENT DOCUMENTS

| | | | |
|---|---|---|---|
| 4,287,200 | 9/1981 | Kawamatsu et al. | 424/270 |
| 4,725,610 | 2/1988 | Meguro et al. | 514/369 |
| 4,775,687 | 10/1988 | Meguro et al. | 514/369 |
| 4,845,231 | 7/1989 | Kees | 548/252 |

FOREIGN PATENT DOCUMENTS

| | | |
|---|---|---|
| 0310370 | 4/1989 | European Pat. Off. . |
| 50-64586 | 5/1980 | Japan . |

OTHER PUBLICATIONS

Musser et al., Journal of Medicinal Chemistry, vol. 33, 1990 pp. 240–245.

Youssefyeh et al., Journal of Medicinal Chemistry, vol. 33, 1990 pp. 1186–1194.

Galemmo, Jr. et al., Journal of Medicinal Chemistry, vol. 33, 1990 pp. 2828–2841.

*Primary Examiner*—David B. Springer
*Attorney, Agent, or Firm*—Wenderoth, Lind & Ponack

[57] ABSTRACT

Novel tetrazole derivatives represented by the formula

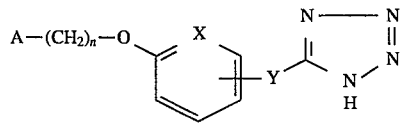

wherein n denotes an integer of 1 to 3; A is an optionally substituted heterocyclic residue; Y is a divalent hydrocarbon residue; and X is CH or N, or pharmaceutically acceptable salts thereof have excellent hypoglycemic and hypolipidemic activities.

26 Claims, No Drawings

TETRAZOLE DERIVATIVES, THEIR PRODUCTION AND USE

This invention relates to a novel tetrazole derivative having the action of lowering blood sugar and lipid in blood, and to an agent comprising it for use in the treatment of diabetes and hyperlipemia.

As remedies for diabetes, various biguanide compounds and sulfonylurea compounds have so far been used. However, biguanide compounds are hardly used at present, since they cause lactic acidosis, while sulfonylurea compounds, which have a strong action of lowering blood sugar, often cause severe hypoglycemia, requiring special attention in use. Tetrazole derivatives having substituents at the 5-position have also been known. For example, in Journal of Medicinal Chemistry, 35, p.944 (1992), it is disclosed that a series of 5-substituted tetrazole derivatives possess blood glucose lowering activity. These compounds, however, are not satisfactory in their activity.

The present inventors made an extensive search for 5-substituted tetrazole derivatives possessing more potent activity of lowering blood glucose and lipid in blood. The inventors found that the introduction of a phenyl group or a pyridyl group substituted with alkoxy group having an optionally substituted heterocyclic residue as the substituent at the 5-position serves to remarkably enhance the activity, thus accomplishing the present invention.

More specifically, the present invention relates to:
(1) a tetrazole derivative of the formula:

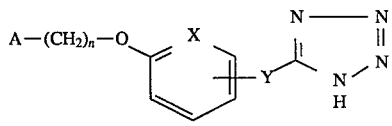

wherein n is an integer of 1 to 3; A is an optionally substituted heterocyclic residue; Y is a divalent hydrocarbon residue; and X is CH or N, or a pharmaceutically acceptable salt thereof;
(2) an agent for the therapy of diabetes or hyperlipemia, which contains, as an effective component, a tetrazole derivative of the formula (I) or a pharmaceutically acceptable salt thereof; and
(3) a method of producing a tetrazole derivative represented by the formula (I), which comprises allowing a compound of the formula:

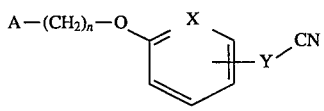

wherein each symbol has the same meaning as defined above to react with a metal azide compound.

In the formula (I), it is preferable that the benzene ring or pyridine ring is substituted with A-(CH$_2$)$_n$—O— at the para-position relative to the attaching point of —Y—.

In the above-mentioned formulas (I) and (II), the heterocyclic residue shown by A preferably is 1) a five-membered ring, 2) a heterocyclic ring having, as the atoms constituting the ring, at least one nitrogen atom, 3) the ring is an aromatic ring having an unsaturated bond, 4) optionally has, as the atoms constituting the ring, two or more nitrogen atoms, and, besides the nitrogen atoms, optionally has hetero-atoms such as oxygen atom and sulfur atom, and 5) may optionally have substituents on optional positions of the ring. Specific examples of the heterocyclic residue shown by A include pyrrolyl(2-pyrrolyl), pyrazolyl(3-pyrazolyl), imidazolyl(2-imidazolyl, 4-imidazolyl), triazolyl(1,2,3-triazol-4-yl, 1,2,4-triazol-3-yl), tetrazolyl, oxazolyl(2-oxazolyl, 4-oxazolyl), and thiazolyl(2-thiazolyl, 4-thiazolyl).

These heterocyclic residues may optionally have one or more substituents on optional positions of the ring. Examples of the substituents include hydrocarbon residues, heterocyclic residues or amino groups, which may optionally have further substituents.

Said hydrocarbon residues include aliphatic hydrocarbon residues, alicyclic hydrocarbon residues, alicyclic-aliphatic hydrocarbons, aromatic-aliphatic hydrocarbon residues and aromatic hydrocarbon residues. Examples of said aliphatic hydrocarbon residues include saturated aliphatic hydrocarbon residues having 1 to 8 carbon atoms such as methyl, ethyl, propyl, isopropyl, butyl, isobutyl, sec.butyl, t.butyl, pentyl, isopentyl, neopentyl, t.pentyl, hexyl, isohexyl, heptyl and octyl; and C$_{2-8}$ unsaturated aliphatic hydrocarbon residues having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propinyl, 2-propinyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. Among them, aliphatic hydrocarbons having at most 4 carbon atoms are preferable. Examples of said alicyclic hydrocarbon residue include saturated alicyclic hydrocarbon residues having 3 to 7 carbon atoms such as cyclopropyl, cyclobutyl, cyclopentyl, cyclohexyl and cycloheptyl; and C$_{5-7}$ unsaturated alicyclic hydrocarbon residues having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. Among them alicyclic hydrocarbon residues having 5 or 6 carbon atoms are preferable. Examples of the alicyclic-aliphatic hydrocarbon residues include, among those formed by bondage of the above-mentioned alicyclic hydrocarbon residues and aliphatic hydrocarbon residues, ones having 4 to 9 carbon atoms such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. Examples of said aromatic aliphatic hydrocarbon residues include phenyl alkyls having 7 to 9 carbon atoms such as benzyl, phenethyl, 1-phenylethyl, 3-phenylpropyl, 2-phenylpropyl and 1-phenylpropyl; and naphthyl alkyl having 11 to 13 carbon atoms such as α-naphthylmethyl, α-naphthylethyl, β-naphthylmethyl and β-naphthylethyl. And, examples of said aromatic hydrocarbon residue include phenyl and naphthyl (α-naphthyl, β-naphthyl).

The said heterocyclic group is a 5- or 6-membered ring which contains, besides carbon atoms, 1 to 3 atoms selected from N, O and S as atoms constituting the ring, which is bonded through a carbon atom. Specific examples of the heterocyclic group include heterocyclic groups such as thienyl (2-thienyl, 3-thienyl), furyl (2-furyl, 3-furyl), pyridyl (2-pyridyl, 3-pyridyl, 4-pyridyl), thiazolyl (2-thiazolyl, 4-thiazolyl, 5-thiazolyl), oxazolyl (2-oxazolyl, 4-oxazolyl, 5-oxazolyl), imidazolyl (2-imidazolyl, 4-imidazolyl, 5-imidazolyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl and 6-pyridazinyl; and a saturated heterocyclic group such as piperidinyl (2-piperidinyl, 3-piperidinyl, 4-piperidinyl), pyrrolidinyl (2-pyrrolidinyl, 3-pyrrolidinyl), morpholinyl (2-morpholinyl), and tetrahydrofuryl (2-tetrahydrofuryl, 3-tetrahydrofuryl etc.).

The amino group may be substituted. As substituted amino group, mention is made of N-mono-substituted amino group and N,N-disubstituted amino group.

"N-mono-substituted amino group" means an amino group having one substituent. Examples of the substituent include a lower alkyl group (e.g. one having 1 to 4 carbon atoms such as methyl, ethyl, propyl, butyl, isobutyl, t.butyl, etc.), cycloalkyl group (e.g. one having 3 to 7 carbon atoms such as cyclopentyl, cyclohexyl, etc.), aryl group (e.g. phenyl, naphthyl, etc.), aromatic heterocyclic group (e.g. pyridyl, thienyl, furyl, oxazolyl, thiazolyl, etc.), non-aromatic heterocyclic group (e.g. piperidinyl, pyrrolidinyl, morpholinyl, etc.), aralkyl group (e.g. benzyl, phenethyl, etc.), acyl group (e.g. acetyl, propionyl, etc.), carbamoyl group, N-mono-substituted carbamoyl group (e.g. N-methylcarbamoyl, N-ethylcarbamoyl, N-propylcarbamoyl, etc.), N,N-disubstituted carbamoyl group (e.g. N,N-dimethylcarbamoyl, N-methyl-N-ethylcarbamoyl, N,N-diethylcarbamoyl, etc.), a lower alkoxycarbonyl group (e.g. one having 2 to 5 carbon atoms such as methoxycarbonyl, ethoxycarbonyl, propoxycarbonyl, etc.), hydroxyl group, a lower alkoxy group (e.g. one having 1 to 4 carbon atoms such as methoxy, ethoxy, propoxy, butoxy, etc.) and aralkyloxy group (e.g. benzyloxy, phenethyloxy, naphthyloxy, etc.).

"N,N-di-substituted amino group" means amino groups having two substituents. Examples of the substituents include, on the one hand, substantially the same ones as in the above-mentioned "N-mono-substituted amino group", while, examples on the other hand include alkyl group, cycloalkyl group, aryl group and aralkyl group. And, in some instances, the two substituents may form a cyclic amino group taken together with nitrogen atom. Examples of such cyclic amino group include 1-azetidiny, 1-pyrrolidino, piperidino, morpholino, piperazino and piperazino having, at the 4-position, e.g. a lower alkyl group (e.g. one having 1 to 4 carbon atoms such as methyl, ethyl, propyl, etc.), an aralkyl group (e.g. benzyl, phenethyl, naphthylmethyl, etc.) or an aryl group (e.g. phenyl, naphthyl, etc.).

The above-mentioned hydrocarbon residue and heterocyclic ring residue as the substituents on the heterocyclic residue A may have a substituent or substituents at their optional positions. When the hydrocarbon residue contains an alicyclic group or when the heterocyclic ring residue is a saturated one, each of them may have one to three lower alkyl groups having 1 to 3 carbon atoms (e.g. methyl, ethyl, propyl and isopropyl) on the ring thereof (including the ring N atoms). And, when the hydrocarbon residue contains an aromatic hydrocarbon residue or when the heterocyclic group is an unsaturated one, it may have 1 to 4 substituents which are the same as or different from one another. Examples of these substituents include halogen (fluorine, chlorine, iodine), hydroxyl, cyano, nitro, trifluoromethyl, a lower alkoxy group (e.g. ones having 1 to 4 carbon atoms such as methoxy, ethoxy, propoxy, isopropoxy and butoxy), a lower alkyl group (e.g. ones having 1 to 4 carbon atoms such as methyl, ethyl, propyl, isopropyl and butyl), a lower alkoxycarbonyl group (e.g. ones having 2 to 4 carbon atoms such as methoxycarbonyl, ethoxycarbonyl and propoxycarbonyl), a lower alkylthio (e.g. ones having 1 to 3 carbon atoms such as methylthio, ethylthio, propylthio and isopropylthio), and a lower alkylamino group (e.g. one having 1 to 4 carbon atoms such as methylamino, ethylamino and dimethylamino).

When the heterocyclic residue shown by A has two or more hydrocarbon residues as substituents thereof, and when these hydrocarbon residues are located at mutually adjacent positions on the aromatic 5-membered heterocyclic ring, they may be combined together to form a condensed ring. This means that the two hydrocarbon residues are bonded to each other to form a saturated or unsaturated di-valent linear hydrocarbon residue having 3 to 5 carbon atoms. Specific examples of the linear hydrocarbon residue include —CH$_2$CH$_2$CH$_2$—, —CH$_2$CH$_2$CH$_2$CH$_2$—, —CH$_2$CH$_2$CH$_2$CH$_2$CH$_2$—, —CH=CHCH$_2$—, —CH=CH—CH=CH—, —CH=CH—CH=CH—CH$_2$— and —CH=CH—CH$_2$CH$_2$CH$_2$—.

Among the heterocyclic residues shown by A, those represented by the formula:

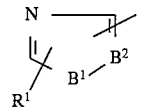

{wherein B$^1$ is a sulfur atom, an oxygen atom or a NR group [wherein R stands for hydrogen, a lower alkyl group (e.g. ones having 1 to 3 carbon atoms such as methyl and ethyl) or an aralkyl group (e.g. benzyl group and phenethyl)]; and B$^2$ is a nitrogen atom or C-R$^2$ (R$^2$ is hydrogen or a lower alkyl group optionally substituted with hydroxyl group); R$^1$ is hydrogen, an optionally substituted hydrocarbon residue or heterocyclic residue; provided that R$^1$ and R$^2$ may be combined with each other to form a condensed ring if R$^1$ is combined with one of ring-constituting carbon atoms adjacent to the carbon atom on which R$^2$ is substituted} are preferable. The hydrocarbon residue, heterocyclic residue shown by R$^1$ and substituents of these groups are the same as those described above referring to aromatic 5-membered heterocyclic residue.

The lower alkyl group shown by R$^2$ is exemplified by ones having 1 to 5 carbon atoms such as methyl, ethyl, propyl, isopropyl, butyl, isobutyl, sec.-butyl, t-butyl and pentyl, with preference given to those having 1 to 3 carbon atoms. Although this alkyl group may have a hydroxyl group at an optional position, the α-position is especially preferred. When B$^2$ is C-R$^2$ and R$^2$ is hydrogen, the ring may be substituted with R$^1$ at the position of B$^2$. This heterocyclic residue is bonded through a relevant atom on the ring, and the group bonded through the carbon atom adjacent to nitrogen atom is preferable. For example, when B$^1$ is NR, B$^2$ is C-R$^2$, and R$^2$ is hydrogen, a group (III) bonded through B$^2$ is also a preferable example.

Among the heterocyclic groups represented by the above formula, especially thiazolyl or oxazolyl represented by the formula:

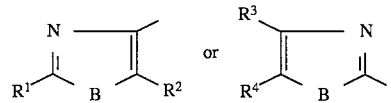

[wherein R$^1$ and R$^2$ have the meanings given above; each of R$^3$ and R$^4$ is hydrogen, an optionally substituted hydrocarbon residue or an optionally substituted heterocyclic residue, and they may form a condensed ring by bonding to each other; and B is an oxygen atom or sulfur atom] is preferable. The hydrocarbon residue or heterocyclic residue shown by R$^3$ or R$^4$ and substituents thereof are the same as those described above referring to an aromatic 5-membered heterocyclic ring residue. R$^3$ and R$^4$ may form a condensed ring, which is the same as the condensed ring formed by an aromatic 5-membered heterocyclic ring residue having two hydrocarbon residues as substituents at mutually adjacent positions.

The ring having X as a component atom is a benzene ring when X is CH, while it is a pyridine ring when X is N. It is preferable that X is CH. The symbol n denotes an integer of 1 to 3, preferably 1 or 2. The divalent hydrocarbon residue shown by Y may be straight-chain or branched, and may be saturated or unsaturated, which includes usually alkylenes and alkenylenes having 1 to 5 carbon atoms. The alkylenes include methylene, 1,1-ethylene, 1,2-ethylene, 1,1-propylene, 1,3-propylene, 1-methyl-1,2-ethylene and 1,4-butylene. The alkenylenes include —CH=CH—CH=CH—, etc. Among them 1,3-propylene and 1,4-butylene are preferable.

The compound (I) of this invention is a compound having acidic nitrogen on its tetrazole ring or having a basic nitrogen when it has a pyridine ring, thus involving basic and acid salts. As these salts, pharmaceutically acceptable one are preferable, which are exemplified by salts with inorganic bases, salts with organic bases, salts with organic acids and salts with basic or acidic amino acids. Preferable examples of salts with inorganic bases include alkali metal salts such as sodium salt or potassium salt; alkaline earth metal salts such as calcium salt or magnesium salt; as well as aluminum salt and ammonium salt. Preferable examples of salts with organic bases include those with trimethylamine, triethylamine, pyridine, picoline, ethanolamine, diethanolamine, triethanolamine, dicyclohexylamine or N,N-dibenzylethylenediamine. Preferable examples of salts include those with hydrochloric acid, hydrobromic acid, nitric acid, sulfuric acid or phosphoric acid. Preferable examples of salts with organic acids include those with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. Preferable examples of salts with basic amino acid include salts with arginine, lysine or ornithine, and, preferable examples of salts with acidic amino acid include salts with aspartic acid or glutamic acid.

The compound (I) or its pharmaceutically acceptable salts of this invention have hypoglycemic activity and low toxicity. For example, when the compound of Example 1 was orally administered to mice at 15 mg/kg for 4 days, no changes occurred in body weight or liver weight, in comparison with the control. And, oral administration of the compound produced in Example 14 at a dose of 100 mg/kg or intraperitoneal administration at a dose of 50 mg/kg killed no test animals. The compounds of this invention can be used for mammals including man as therapeutic agents for diabetes and hyperlipemia. The compound (I) can be administered orally or non-orally as solid compositions such as tablets, capsules, granules or powders; or liquid compositions such as syrup or injections, prepared by formulating with pharmaceutically acceptable carriers.

As pharmaceutically acceptable carriers, use is made of conventional organic or inorganic carriers for pharmaceutical preparations, more specifically, for example, excipients, lubricants, binders and disintegrators for solid preparations; and solvents, solubilizers, suspending agents, isotonizers, buffering agents and local anesthetic agents. And, upon necessity, such additives as antiseptics, antioxidants, colorants and sweeteners are further used. Preferable examples of excipients include lactose, sucrose, D-mannitol, starch, crystalline cellulose and light silicon dioxide. Preferable examples of lubricants include magnesium stearate, calcium stearate, talc and colloid silica. Preferable examples of binders include crystalline cellulose, sugar, D-mannitol, dextrin, hydroxypropyl cellulose, hydroxypropyl methyl cellulose and polyvinylpyrrolidone. Preferable examples of disintegrators include starch, carboxymethyl cellulose, carboxymethyl cellulose calcium, cross carmellose sodium and carboxymethyl starch sodium. Preferable examples of solvents include distilled water for injection, alcohol, propylene glycol, macrogol, sesame oil and corn oil. Preferable examples of solubilizers include polyethylene glycol, propylene glycol, D-mannitol, benzyl benzoate, ethanol, trisamino methane, cholesterol, triethanolamine, sodium carbonate and sodium citrate. Preferable examples of suspending agents include surfactants such as stearyl triethanolamine, sodium lauryl sulfate, lauryl aminopropionate, lecithin, benzalkonium chloride, benzethonium chloride, glycerine monostearate; and hydrophilic polymers such as poly (vinyl alcohol), polyvinylpyrrolidone, carboxymethyl cellulose sodium, methylcellulose, hydroxymethylcellulose, hydroxyethylcellulose and hydroxypropylcellulose. Preferable examples of isotonizers include sodium chloride, glycerine and D-mannitol. Preferable examples of buffering agents include buffer solutions of phosphates, acetates, carbonates and citrates. Preferable examples of local anesthetic agents include benzyl alcohol. Preferable examples of antiseptics include paraoxybenzoic acid esters, chlorobutanol, benzyl alcohol, phenethyl alcohol, dehydroacetic acid and sorbic acid. Preferable examples of anti-oxidants include sulfites and ascorbic acid.

Concerning the method of administration, the compound (I) is normally used orally in the form of, for example, tablets, capsules (including soft capsules and microcapsules), powders and granules, but, as the case may be, it can be administered non-orally in the form of, for example, injectable preparations, suppositories and pellets. Daily dose for oral administration in adults ranges from 0.05 to 10 mg/kg/, preferably divided into one to three doses daily.

The following is the description of the method of producing the compound (I) of this invention.

(Method A)

By allowing a nitrile derivative (II) to react with an azide compound, a tetrazole derivative (I) is produced. The reaction from (II) to (I) is conducted, for example, in accordance with the method described on the Journal of American Chemical Society, 80, p.3908 (1958), allowing (II) to react with sodium azideammonium chloride in N,N-dimethylformamide. The respective amounts of ammonium chloride and sodium azide range from 1 to 7 moles, preferably from 1 to 5 moles, relative to one mole of the compound (II). This reaction is carried out at temperatures ranging from 50° C. to 180° C. for 1 to 50 hours. And, the reaction from (II) to (I) can also be conducted by, for example, in accordance with the method described on the Journal of Organic Chemistry 56., p.2395 (1991), allowing the compound (II) to react with trimethyltin azide or tributyltin azide, followed by treatment with an acid.

The tetrazole derivatives and their salts thus obtained can be isolated and purified by known means of separation and purification such as concentration, concentration under reduced pressure, crystallization, recrystallization, phasic transfer and chromatography.

(Method B)

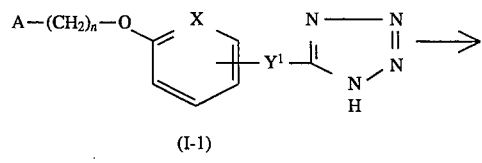

(I-1)

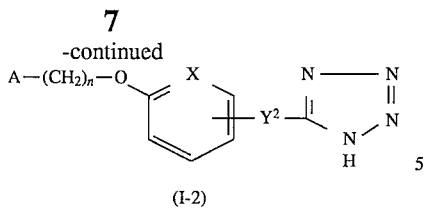

(I-2)

[wherein $Y^1$ is an unsaturated divalent hydrocarbon residue, $Y^2$ is a saturated divalent hydrocarbon residue, and other symbols are of the same meaning as defined above.]

The unsaturated divalent hydrocarbon residue shown by $Y^1$ is unsaturated one shown by Y, and the saturated divalent hydrocarbon residue shown by $Y^2$ is saturated one shown by Y.

In this method, the compound (I-1) among the compounds produced by Method A is subjected to reduction to produce the compound (I-2). While this reduction reaction can be conducted by a per se known method, it is carried out advantageously by catalytic hydrogenation using a metal catalyst. This catalytic hydrogenation is carried out, in accordance with a conventional method, in a solvent in the presence of a catalyst under hydrogen atmosphere of 1 to 150 atmospheric pressure. Examples of the solvent include alcohols such as methanol, ethanol, propanol, isopropanol and 2-methoxyethanol, aromatic hydrocarbons such as benzene, toluene and xylene, ethers such as ethyl ether, isopropyl ether, dioxane and tetrahydrofuran, halogenated hydrocarbons such as chloroform, dichloromethane and 1,1,2,2-tetrachloroethane, ethyl acetate, acetic acid or a mixture of these solvents. As the catalyst, use is made of, for example, a transition metal such as palladium, platinum or rhodium to have the reaction proceed advantageously. The reaction temperatures range from 0° to 100° C., preferably 10° to 80° C., and the reaction time ranges from 0.5 to 50 hours.

Thus-obtained tetrazole derivatives and salts thereof can be isolated and purified by means of conventional means such as concentration, concentration under reduced pressure, crystallization, recrystallization, phasic transfer and chromatography.

The nitrile derivatives (II) employed as the starting materials in the method of this invention can be produced by, for example, the following method.

(Method C)

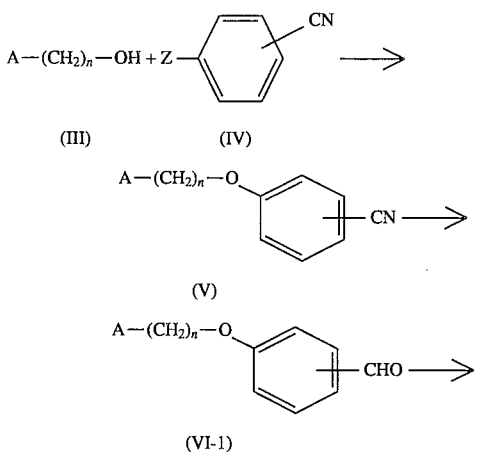

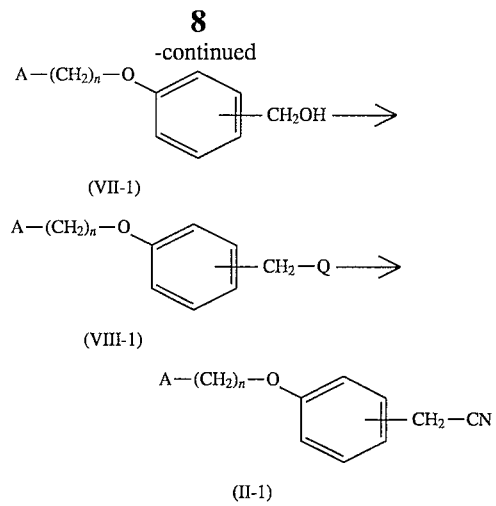

[in the formula (IV), Z stands for a halogen atom, in the formula (VIII-1), Q stands for a leaving group, and other symbols are of the same meaning as defined above].

As the halogen atom shown by Z, mention is made of fluorine, chlorine, bromine and iodine. As the leaving group shown by Q, mention is made of, for example, besides halogen atoms including chlorine, bromine and iodine, methanesulfonyloxy and p-toluenesulfonyloxy, among others.

The production steps comprising condensation of the compound (III) with the compound (IV) to give the compound (V), which is then led to the aldehyde derivative (VI-I), are conducted in accordance with the methods described in, for example, the Chemical and Pharmaceutical Bulletin, 39, p.1440 (1991) and the Journal of Medicinal Chemistry, 35, p.2617 (1992).

Then, the compound (VI-1) is subjected to reduction to produce the alcohol compound (VII-1). This reduction can be conducted by a per se known method, for example, reduction by using a metal hydride, reduction by using a metal hydride complex, reduction by using diborane and a substituted borane and catalytic hydrogenation. In other words, this reaction is carried out by processing the compound (VI-1) with a reducing agent. Examples of the reducing agent include a metal hydride complex such as alkali metal borohydride (e.g. sodium borohydride and lithium borohydride); a metal hydride complex such as lithium aluminum hydride; a metal hydride such as sodium hydride; a metal or a metal salt such as an organotin compound (e.g. triphenyltin hydride), a nickel compound and a zinc compound; a catalytic reduction agent using a transition metal catalyst such as palladium, platinum and rhodium, and hydrogen; and diborane, among others. This reaction is conducted in an organic solvent which does not affect on the reaction. As the solvent, use is made of by adequately selecting, depending of kinds of the reducing agent, from, for example, aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a mixture of these solvents. The reaction temperatures range from −20° C. to 150° C., especially preferably from 0° C. to 100° C. The reaction time ranges from about 1 to 24 hours.

Then, the compound (VII-1) is allowed to react with a halogenating agent or a sulfonylating agent to produce the compound (VIII-1). As the halogenating agent, use is preferably made of, for example, hydrochloric acid, thionyl chloride and phosphorus tribromide, and in this case, the compound (VIII-1), wherein Q stands for chlorine or bromine, is produced. This reaction is conducted in an adequate inert solvent (e.g. benzene, toluene, xylene, chloroform and dichloromethane) or by using an excess amount of a halogenating agent as the solvent at temperatures ranging from −10° to 80° C. The amount of the halogenating agent to be employed ranges from 1 to 20 mol. relative to the compound (VII-1). As the sulfonylating agent, use is preferably made of, for example, methanesulfonyl chloride, p-tosyl chloride and benzenesulfonyl chloride, to produce the compound (VIII-1) wherein Q stands for methanesulfonyloxy, p-toluenesulfonyloxy and benzenesulfonyloxy, respectively. This reaction is conducted in an adequate inert solvent (e.g. benzene, toluene, xylene, ethyl ether, ethyl acetate, tetrahydrofuran, chloroform and dichloromethane) in the presence of a base (e.g. triethylamine, N-methyl morpholine, sodium hydrogencarbonate, potassium hydrogencarbonate, sodium carbonate and potassium carbonate) at temperatures ranging from −10° to 30° C. The amounts of the sulfonylating agent and the base range from 1 to 2 mol. relative to 1 mol. of the compound (VII-1), respectively. By allowing 1 mol. of the compound (VIII-1), wherein Q stands for chlorine, bromine or sulfonyloxy, to react with 1 to 1.5 mol. of sodium iodide or potassium iodide, the compound (VIII-1), wherein Q stands for iodine, can also be produced. In this case, the reaction can be conducted in a solvent such as acetone, methyl ethyl ketone, methanol and ethanol at temperatures ranging from 20° to 80° C. Then, by allowing the compound (VIII-1) to react with potassium cyanide or sodium cyanide to produce the compound (II-1). The reaction is conducted usually in a solvent (e.g. ether, tetrahydrofuran, dioxane, chloroform, dichloromethane, 1,2-dichloroethane, methanol, ethanol, ethyl acetate, acetone, 2-butanone, N,N-dimethylformamide and dimethyl sulfoxide) at temperatures ranging from 0° C. to 100° C. The amount of potassium cyanide or sodium cyanide to be employed ranges from 1 to 8 mol. relative to 1 mol. of the compound (VIII-1).

The nitrile derivative (II-1) thus obtained can be isolated and purified by means of a conventional isolating and purifying procedures, for example, concentration, concentration under reduced pressure, crystallization, recrystallization, phasic transfer and chromatography.

(Method D)

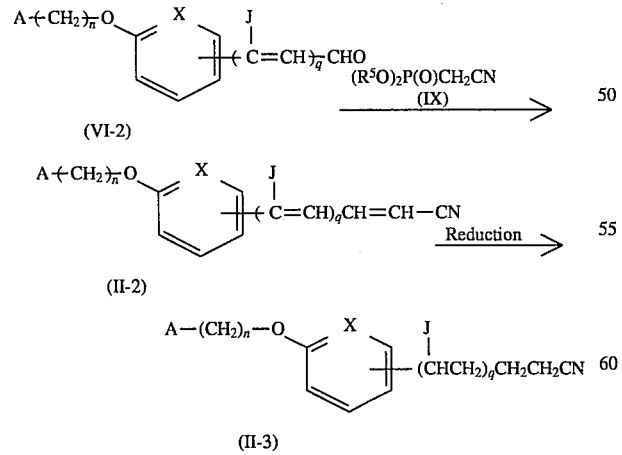

[wherein J is a hydrogen or a lower alkyl group, $R^5$ stands for a lower alkyl group, q denotes 0 or 1 and other symbols are of the same meaning as defined above.]

Examples of the lower alkyl group shown by J or $R^5$ include ones having 1 to 4 carbon atoms such as methyl, ethyl, propyl, isopropyl and butyl etc.

In this method, an aldehyde derivative (VI-2) is allowed to react with a cyanomethylphosphonic acid ester derivative (IX) to produce an unsaturated nitrile derivative (II-2). The reaction of (VI-2) with (IX) is conducted, in accordance with a conventional manner, in an adequate solvent in the presence of a base. Examples of the solvent include aromatic hydrocarbons such as benzene, toluene and xylene; ethers such as dioxane, tetrahydrofuran and dimethoxyethane; alcohols such as methanol, ethanol and propanol; N,N-dimethylformamide, dimethyl sulfoxide, chloroform, dichloromethane, 1,2-dichloroethane, 1,1,2,2-tetrachloroethane and a mixture of these solvents. Examples of the base include alkali metal salts such as sodium hydroxide, potassium hydroxide, potassium carbonate, sodium carbonate and sodium hydrogencarbonate; amines such as pyridine, triethylamine, N,N-dimethylaniline; metal hydrides such as sodium hydride and potassium hydride; sodium ethoxide, sodium methoxide and potassium t-butoxide, and the amount of these bases to be employed ranges from 1 to 5 mol. equivalents relative to the compound (VI-2). The amount of the compound (IX) to be employed ranges from 1 to 5 mol. equivalents, preferably from about 1 to 3 mol. equivalents, relative to the compound (VI-2). This reaction is conducted usually at temperatures ranging from −50° C. to 150° C., preferably from about −10° to 100° C. The reaction time ranges from 0.5 to 30 hours. By subjecting the compound (II-2) thus obtained to reduction, the compound (II-3) is produced. This reduction is conducted in substantially the same manner as in Method B.

The nitrile derivatives thus obtained can be isolated and purified by means of a conventional isolating and purifying procedures such as concentration, concentration under reduced pressure, solvent extraction, crystallization, recrystallization, phasic transfer and chromatography.

[Method E]

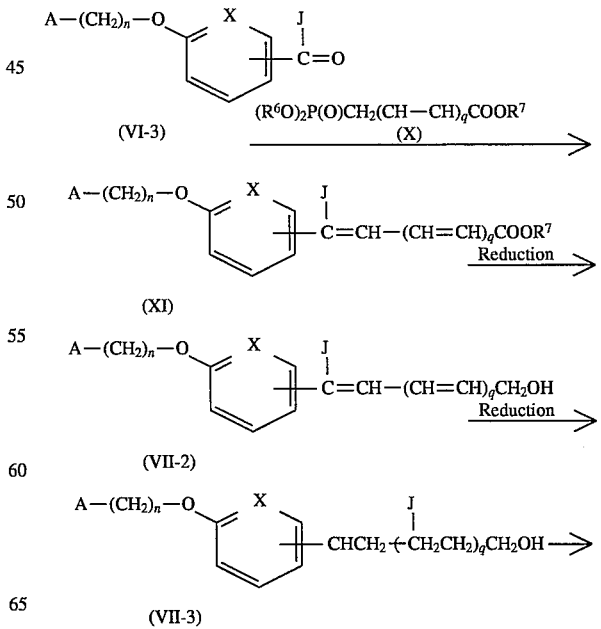

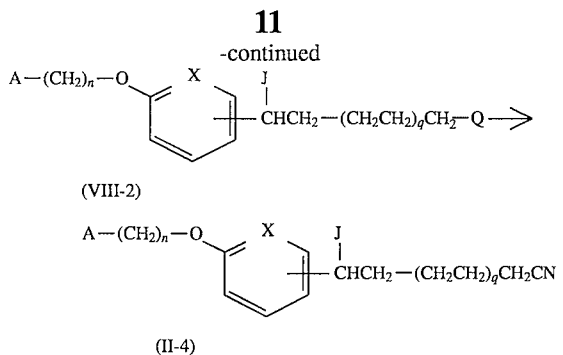

(VIII-2)

(II-4)

[wherein $R^6$ and $R^7$ independently stand for a lower alkyl group; q denotes 0 or 1; and other symbols are of the same meaning as defined above.]

Examples of the lower alkyl group shown by $R^6$ and $R^7$ include ones having 1 to 4 carbon atoms such as methyl, ethyl, propyl, isopropyl and butyl etc.

In this method, at first, an aldehyde or a ketone derivative (VI-3) is allowed to react with a phosphonoacetic acid derivative or γ-phosphonocrotonic acid derivative (X) to produce an unsaturated ester derivative (XI). The reaction of (VI-3) with (X) is carried out in substantially the same manner as in the reaction of the compound (VI-2) with (IX) in Method D. Then, the compound (XI) is subjected to reduction to produce the alcohol derivative (VII-2). This reduction reaction can be carried out by a per se known method as exemplified by reduction with a metal hydride, reduction with a metal hydride complex and reduction with diborane and substituted borane. In other words, this reaction is conducted by processing the compound (XI) with a reducing agent. As the reducing agent, mention is made of, for example, a metal hydride complex such as alkali metal borohydride (e.g. sodium borohydride and lithium borohydride) and lithium aluminum hydride, and diborane, and the reaction is more advantageously carried out by using diisobutylaluminum hydride. This reaction is carried out in an organic solvent which does not exert influence on the reaction. As the solvent, use is made of by adequately selecting, depending of kinds of the reducing agent, from, for example, aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a mixed solvent of them. The reaction temperatures range from −20° C. to 150° C., especially preferably from 0° C. to 100° C. The reaction time ranges from about 1 to 24 hours. Then, by subjecting the compound (VII-2) to reduction, the compound (VII-3) is produced. This reduction reaction is carried out in substantially the same manner as in Method B. The compound (VII-3) is processed, in substantially the same manner as in Method C comprising leading the compound (VII-1) to (VIII-1) and further to (II-1), to produce the nitrile derivative (II-4).

The nitrile derivatives thus obtained can be isolated and purified by conventional isolating and purifying means such as concentration, concentration under reduced pressure, solvent extraction, crystallization, recrystallization, phasic transfer and chromatography.

The pyridine aldehyde derivatives (VI-4) to be employed in Method D and Method E can be produced in accordance with, for example, Method F.

[Method F]

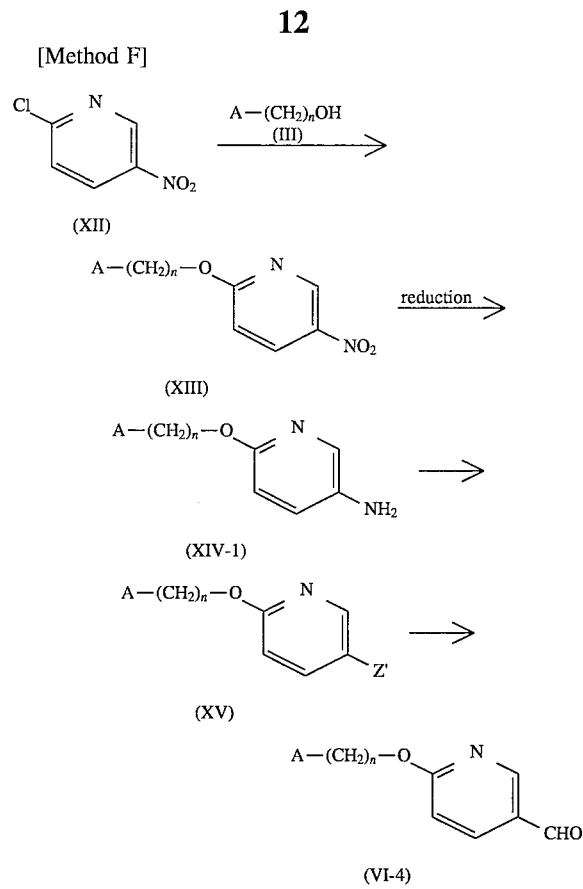

[in the formula (XV), Z' stands for chlorine, bromine or iodine, and other symbols are of the same meaning as defined above.]

In this method, at first, 2-chloro-5-nitropyridine (XII) is allowed to react with the alcohol derivative (III) to produce the compound (XIII). The reaction of (XII) with (III) is conducted, in accordance with a conventional method, in an adequate solvent in the presence of a base. Examples of the solvent include aromatic hydrocarbons such as benzene, toluene and xylene; ethers such as dioxane, tetrahydrofuran and dimethoxyethane; N,N-dimethylformamide, dimethyl sulfoxide, chloroform, dichloromethane, 1,2-dichloroethane, 1,1,2,2-tetrachloroethane; and a mixture solvent of them. Examples of the base include alkali metal salts such as sodium hydroxide, potassium hydroxide, potassium carbonate, sodium carbonate and sodium hydrogencarbonate; amines such as pyridine, triethylamine, and N,N-dimethyl aniline; metal hydrides such as sodium hydride and potassium hydride; potassium t-butoxide, etc., and the amount of these bases to be employed is preferably about 1 to 5 mol. equivalents relative to the compound (III). This reaction is carried out usually at temperatures ranging from −50° C. to 150° C., preferably from about −10° C. to 100° C. The reaction time ranges from 0.5 to 30 hours. Then the compound (XIII) is subjected to reduction to produce the amine derivative (XIV-1). While this reduction can be carried out by a per se known method, it is advantageously carried out by catalytic hydrogenation using a metal catalyst. This catalytic hydrogenation is carried out, in accordance with a conventional method, in an solvent in the presence of a catalyst under hydrogen atmosphere of 1 to 150 atm. Examples of the solvent include alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; halogenated hydrocarbons such as chloroform, dichloromethane and 1,1,2,2-tetrachloroethane; ethyl acetate, acetic acid; or a mixed solvent of them. Use of, as the catalyst, for example, a metal such as a nickel compound, and a transition metal catalyst such as palladium, platinum and rhodium, serves to allow the reaction to proceed advantageously. The reaction temperatures range from 0° to 100° C., preferably from 10° to 80° C., and the reaction time ranges from 0.5 to 50 hours. Then, the compound (XIV-1) is subjected to a per se known the Sandmeyer reaction to produce the halogen derivative (XV). In this reaction, at first, the compound (XIV-1) is diazotized by adding dropwise thereto an aqueous solution of sodium nitrite ($NaNO_2$) in a solvent in the presence of hydrochloric acid, hydrobromic acid or hydroiodic acid, which is then allowed to react with an aqueous solution of sodium halide or potassium halide to produce the compound (XV). Examples of the solvent include alcohols such as methanol, ethanol, propanol, isopropanol and 2-methoxyethanol; ethers such as dioxane and tetrahydrofuran; acetone, 2-butanone, or a mixed solvent of them. The reaction temperatures range from −80° C. to 100° C., preferably from −50° to 60° C., and the reaction time ranges from 0.5 to 50 hours. Then, the compound (XV) is processed with, for example, butyllithium, tert.butyllithium, methyllithium, phenyllithium or phenylmagnesium bromide to give a lithio compound, which is then allowed to react with N,N-dimethylformamide (DMF) to produce the compound (Method G)

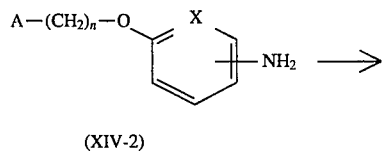

(XIV-2)

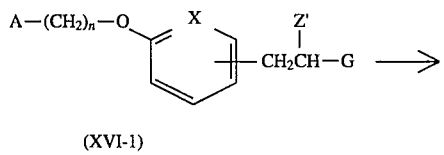

(XVI-1)

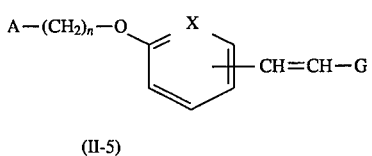

(II-5)

[in the formulae (XVI-1) and (II-5), G stands for cyano group (CN) or $COOR_7$; and other symbols are of the same meaning as defined above.].

The reaction from the compound (XIV-2) to the compound (XVI-1) is conducted in accordance with the method described in the Journal of Medicinal Chemistry, 35, p.2617 (1992). More specifically, the compound (XIV-2) is subjected to so called Meerwein arylation reaction, which comprises diazotizing the compound (XIV-2) in the presence of hydrohalogenic acid (HZ'), which is further allowed to react with acrylic acid ester ($CH_2=CHCOOR^7$) or acrylonitrile ($CH_2=CHCN$) in the presence of a copper catalyst (e.g. copper (I) oxide, copper (II) oxide, copper (I) chloride, copper (II) chloride, copper (I) bromide and copper (II) bromide). Then, the compound (XVI-1) is subjected to dehydrohalogenation to produce the compound (II-5). This dehydrohalogenation reaction is conducted in an adequate solvent in the presence of a base. Examples of the solvent include aromatic hydrocarbon such as benzene, toluene and xylene; ethers such as dioxane, tetrahydrofuran and dimethoxyethane; alcohols such as methanol, ethanol and propanol; ethyl acetate, acetonitrile, pyridine, N,N-dimethylformamide, dimethyl sulfoxide, chloroform, dichloromethane, 1,2-dichloroethane, 1,1,2,2-tetrachloroethane, acetone and 2-butanone; and a mixed solvent of them. Examples of the base include inorganic bases such as alkali metal hydroxide (e.g. sodium hydroxide and potassium hydroxide), alkaline earth metal hydroxide (e.g. magnesium hydroxide and calcium hydroxide), alkali metal carbonate (e.g. sodium carbonate and potassium carbonate), alkaline earth metal carbonate (e.g. magnesium carbonate and calcium carbonate), alkali metal hydrogencarbonate (sodium hydrogencarbonate and potassium hydrogencarbonate) and alkali metal acetate (sodium acetate and potassium acetate); and organic bases such as trialkylamine (e.g. trimethylamine and triethylamine), picoline, N-methylpyrrolidine, N-methylmorpholine, 1,5-diazabicyclo[4,3,0]non-5-ene, 1,4-diazabicyclo[2,2,2]non-5-ene and 1,8-diazabicyclo [5,4,0]-7-undecene. The amount of these bases to be employed ranges preferably from about 1 to 5 mol. equivalents relative to the compound (XVI-1). This reaction is carried out usually at temperatures ranging from −20° C. to 150° C., preferably from about −10° C. to 120° C.

(Method H)

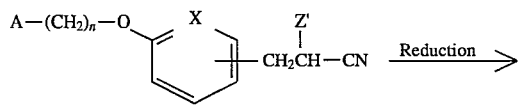

(XVI-2)

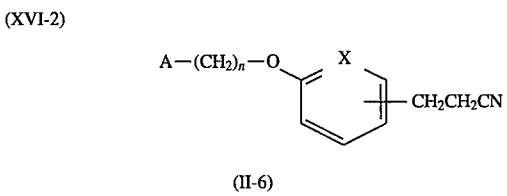

(II-6)

[wherein each symbol is of the same meaning as defined above.]

In this method, α-halogenopropionitrile derivative (XVI-2) is subjected to reduction to produce the propionitrile derivative (II-6). This method can be carried out by, for example, catalytic reduction in substantially the same manner as in Method B, or a conventional method using zinc or iron and acetic acid.

(Method I)

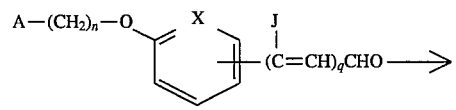

(VI-2)

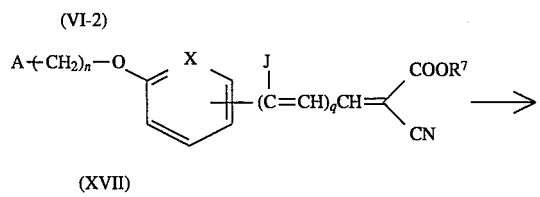

(XVII)

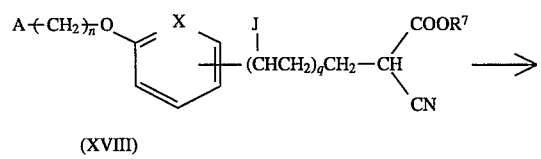

(XVIII)

-continued

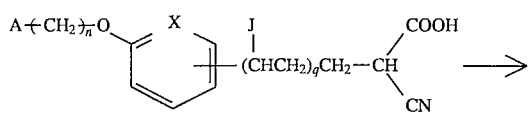

(XIX)

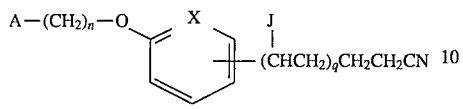

(II-3)

[wherein each symbol is of the same meaning as defined above.]

In this method, at first, the compound (VI-2) and a cyanoacetic acid ester derivative are subjected to condensation to produce the compound (XVII). This condensation reaction is carried out in a solvent in the presence of a base. Examples of the solvent include alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; pyridine, N,N-dimethylformamide, dimethyl sulfoxide and acetic acid. Examples of the base to be employed include sodium alkoxide (e.g. sodium methoxide and sodium ethoxide), potassium carbonate, sodium carbonate, sodium hydride, sodium acetate, or secondary amines such as piperazine, pyrrolidine, morpholine, diethylamine and diisopropylamine, etc.. The amount of the base to be used ranges from 0.01 to 5 molar equivalents, preferably from 0.05 to 2 molar equivalents relative to the compound (VI-2). This reaction is carried out at temperatures ranging from 0° to 150° C., preferably from 20° to 120° C. for a period ranging from 5 to 30 hours. Then, the compound (XVII) is subjected to reduction to produce the compound (XVIII). This reduction reaction can be carried out by a per se known method, for example, reduction using a metal hydride, reduction using a metal hydride complex or catalytic hydrogenation. In other words, this reaction is carried out processing the compound (XVII) with a reducing agent. Examples of the reducing agent include a metal hydride complex such as alkali metal borohydride (e.g. sodium borohydride and lithium borohydride); a metal hydride complex such as lithium aluminum hydride; a metal hydride such as sodium hydride; a metal or a metal salt such as an organotin compound (e.g. triphenyltin hydride), a nickel compound and a zinc compound; a catalytic reduction agent using a transition metal catalyst such as palladium, platinum and rhodium, and hydrogen; and diborane, among others. Above all, use of alkali metal borohydride (e.g. sodium borohydride and lithium borohydride) serves to allow the reaction to proceed advantageously. This reaction is conducted in an organic solvent which does not affect on the reaction. As the solvent, use is made of by adequately selecting, depending of kinds of the reducing agent, from, for example, aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a mixture of these solvents. The reaction temperatures range from −20° C. to 150° C., especially preferably from 0° C. to 100° C. The reaction time ranges from about 1 to 24 hours. Then, the compound (XVIII) is subjected to hydrolysis, which is then subjected to decarboxylation to produce the compound (II-3). This hydrolysis is carried out, in accordance with a per se known method, in an aqueous solvent in the presence of an acid or a base. The carboxylic acid derivative (XIX) thus obtained is subjected to decarboxylation, after isolation or without isolation, to produce the compound (II-3). This decarboxylation reaction is carried out in a solvent with heating. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; chlorobenzene, o-dichlorobenzene and pyridine; or a mixed solvent of them. The reaction temperature ranges from 50° C. to 250° C., especially preferably from 70° C. to 160° C. The reaction time ranges from about 1 to 24 hours.

A nitrile derivative can also be produced by method J or method K.

(Method J)

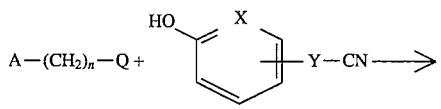

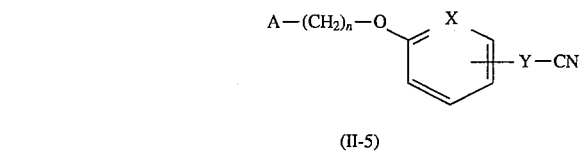

(II-5)

[wherein each symbol has the meaning given above]

In this method, a nitrile derivative (II-5) can be produced by the reaction of a compound (XX) with a compound (XXI). The method is carried out in a suitable solvent in the presence of a base. The solvents include aromatic hydrocarbons such as benzene, toluence, xylene, etc. ethers such as dioxane, tetrahydrofuran, dimethoxyethane, etc., alcohols such as methanol, ethanol, propanol, etc. halogenated hydrocarbons such as chloroform, dichloromethane, 1,2-dichloroethane, 1,1,2,2-tetrachloroethane, etc., N,N-dimethylformamide, dimethyl sulfoxide, or a mixture of two or more selected from these solvents. As the base, alkali metal salts such as sodium hydroxide, potassium hydroxide, potassium carbonate, sodium carbonate, sodium hydrogencarbonate, etc., amines such as pyridine, triethylamine, N,N-dimethylaniline, etc., metal hydride such as sodium hydride, potassium hydride, etc., metal alkoxide such as sodium ethoxide, sodium methoxide, potassium t-butoxide, etc. are mentioned. The base is used in an amount of 1 to 5 mol per 1 mol of compound (III). This reaction is carried out at a temperature ranging from −50° C. to 150° C., preferably −10° C. to 100° C. The reaction time is usually 0.5 to 30 hours.

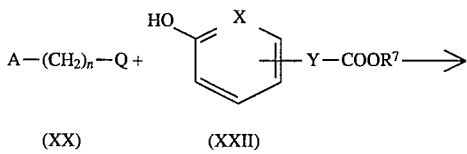

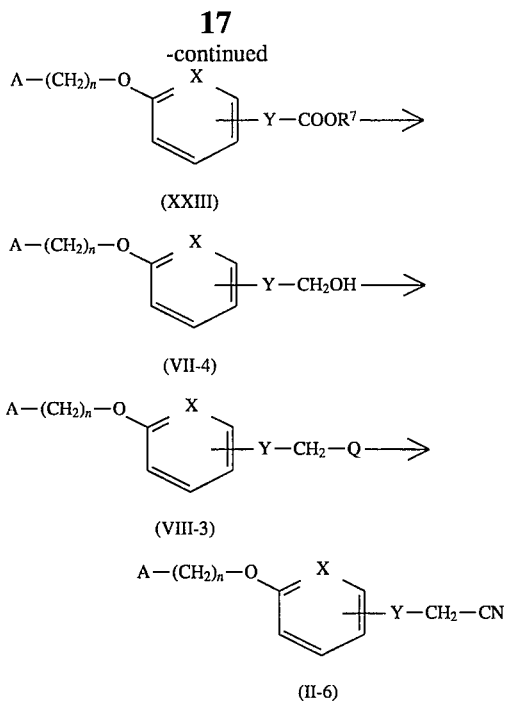

In this method, first a compound (XX) and a compound derivative (XXII) is reacted to give an ester derivative (XXIII). This reaction is carried out in a manner similar to that of a compound (XX) and a compound (XXI) in Method J. Then a compound (XIII) is converted to alcohol derivative (VII-4) by a manner similar to the reaction converting a compound (XI) to a compound (VII-2) in Method E. A compound (VII-4) is converted to a compound (VIII-3) by a manner similar to the reaction converting a compound (VII-3) to a compound (VIII-2) in Method E. A compound (VIII-3) is converted to a compound (II-6) by a manner similar to the reaction converting a compound (VIII-2) to a compound (II-4) in Method E.

The compound (I) of this invention has hypoglycemic and hypolipidemic actions. Experimental data supporting these actions are as follows.

Experimental Example

Hypoglycemic and hypolipidemic actions in mice

The test compound mixed with powdered diet (CE-2, Japan Clea) at a ratio of 0.01% or 0.005% was fed to KKA$^y$ mice (9–14 week old) for 4 days ad libitum. The animals had free access to water during this period. Blood was collected from the orbital venous plexus and the values of plasm glucose and triglyceride were respectively determined quantitatively by enzyme method using Iatrochem-GLU(A) and Iatro-MA701 TG kit (Iatron). The respective values are shown in terms of percent reduction compared to non-drug-dosed group, as shown in [Table 1].

TABLE 1

| Compound (Example No.) | Dose[1] | Hypoglycemic Action (%) | Hypolipidemic Action (%) |
|---|---|---|---|
| 1 | 0.01 | 45 | 28 |
| 2 | 0.01 | 21 | 9 |
| 3 | 0.01 | 15 | 26 |
| 5 | 0.01 | 26 | 10 |
| 7 | 0.01 | 36 | 37 |
| 8 | 0.01 | 38 | 32 |

TABLE 1-continued

| Compound (Example No.) | Dose[1] | Hypoglycemic Action (%) | Hypolipidemic Action (%) |
|---|---|---|---|
| 9 | 0.01 | 31 | 33 |
| 14 | 0.005 | 53 | 74 |
| 16 | 0.005 | 43 | 48 |
| 22 | 0.005 | 46 | 85 |
| 23 | 0.005 | 26 | 23 |

[1]Concentration (%) (w/w) of the test compound in diet.

As stated above, tetrazole derivatives (I) of the present invention exhibit excellent hypoglycemic and hypolipidemic action, and are useful as a therapeutic agent for diabetes mellitus, hyperlipemia, hypertension or the like.

Reference Example 1

To a solution of 2-chloro-5-nitropyridine (25 g) and 2-(5-methyl-2-phenyl-4-oxazolyl)ethanol (32.1 g) in THF (250 ml) was added, in small portions, sodium hydride (60% in oil, 6.92 g), and the mixture was stirred. The reaction mixture was stirred, at room temperature, for further 15 hours, which was poured into water, followed by extraction with ethyl acetate. The ethyl acetate layer was washed with water and dried (MgSO$_4$), then the solvent was distilled off under reduced pressure. The residual crystals are collected by filtration, followed by recrystallization from ethanol to afford 2-[2-(5-methyl-2-phenyl-4-oxazolyl)ethoxy]-5-nitropyridine (25.4 g, 49%) as yellowish brown crystals, m.p.110.5°–111.5° C.

Reference Example 2

A mixture of 2-[2-(5-methyl-2-phenyl-4-oxazolyl)ethoxy]-5-nitropyridine (13.4 g), palladium carbon (5%, 1.5 g) and ethyl acetate (200 ml) methanol (150 ml) was subjected to catalytic hydrogenation at room temperature under 1 atmospheric pressure. The catalyst was filtered off, and the filtrate was concentrated under reduced pressure to leave crystals. The crystals were collected by filtration to obtain 5-amino-2-[2-(5-methyl-2-phenyl-4-oxazolyl)ethoxy]pyridine (11.4 g, 93%), which was recrystallized from ethyl acetate—hexane to give brown crystals, m.p.107°–108° C.

Reference Example 3

To a mixture of 5-amino-2-[2-(5-methyl-2-phenyl-4-oxazolyl)ethoxy]pyridine (10.0 g), conc. hydrochloric acid (8.47 ml) and acetone (100 ml) was added dropwise, at temperatures of 10° C. or below, a solution of sodium nitrite (NaNO$_2$) (2.46 g) in water (10 ml). The mixture was stirred for 30 minutes at 10° C., to which was added dropwise a solution of potassium iodide (KI) (2.46 g) in water (10 ml). The reaction mixture was stirred for one hour at 30°–35° C., and for one hour at 35°–40° C., followed by concentration under reduced pressure. The residue was poured into water, which was subjected to extraction with ethyl acetate. The ethyl acetate layer was washed with water and dried (MgSO$_4$), then the solvent was distilled off under reduced pressure to leave an oily product, which was subjected to a silica gel column chromatography. From the fraction eluted with ethyl acetate—hexane (1:3, v/v), 5-iodo-2-[2-(5-methyl-2-phenyl-4-oxazolyl)ethoxy]pyridine (7.22 g, 52%), which was recrystallized from ethyl acetate—hexane to yield colorless crystals, m.p.105°–106° C.

Reference Example 4

To a solution of 5-iodo-2-[2-(5-methyl-2-phenyl-4-oxazolyl)ethoxy]pyridine (2.5 g) in tetrahydrofuran (40 ml) was added dropwise, at −65° C. in nitrogen streams, a hexane solution of n-butyl lithium (1.6M, 4.61 ml). The mixture was stirred for 15 minutes at the same temperature, to which was added dropwise N,N-dimethylformamide (0.71 ml). The cooling bath was removed, and the reaction mixture was stirred for further 30 minutes, to which was added a saturated aqueous solution of ammonium chloride (6 ml). The reaction mixture was poured into water, which was subjected to extraction with ethyl acetate. The ethyl acetate layer was washed with water and dried (MgSO$_4$), then the solvent was distilled off under reduced pressure to leave 5-formyl-2-[2-(5-methyl-2-phenyl-4-oxazolyl)ethoxy]pyridine (1.5 g, 79%), which was recrystallized from ethyl acetate—hexane to give colorless crystals, m.p.99°–100° C.

Reference Example 5

To a solution of 4-[2-(5-methyl-2-phenyl-4-oxazolyl)ethoxy]benzaldehyde (7.0 g) in ethanol (100 ml) was added, under ice-cooling, sodium borohydride (0.473 g), and the mixture was stirred for 2 hours at room temperature. To the reaction mixture was added acetic acid (2 ml), which was poured into ice-water, then resulting crystalline precipitate was collected by filtration, followed by recrystallization from ethyl acetate—hexane to yield 4-[2-(5-methyl-2-phenyl-4-oxazolyl)ethoxy]benzyl alcohol (6.9 g, 88%) as colorless plates, m.p.112°–113° C.

Reference Example 6

To a solution of 4-[2-(5-methyl-2-phenyl-4-oxazolyl)ethoxy]benzyl alcohol (6.8 g) in chloroform (100 ml) was added thionyl chloride (3.1 g), and the mixture was stirred for one hour at room temperature. The reaction mixture was washed with a saturated aqueous solution of sodium hydrogencarbonate and then water, followed by drying (MgSO$_4$). The solvent was distilled off to leave 4-[2-(5-methyl-2-phenyl-4-oxazolyl)ethoxy]benzyl chloride (6.5 g, 90%) as colorless needles, m.p.93°–94° C.

Reference Example 7

A mixture of 4-[2-(5-methyl-2-phenyl-4-oxazolyl)ethoxy]benzyl chloride (6.4 g), powdered potassium cyanide (4.0 g) and N,N-dimethylformamide (50 ml) was stirred for two hours at 60° C. The reaction mixture was poured into water, which was subjected to extraction with ethyl acetate. The ethyl acetate layer was washed with water and dried (MgSO$_4$), then the solvent was distilled off to leave 4-[2-(5-methyl-2-phenyl-4-oxazolyl)ethoxy]benzyl cyanide (5.2 g, 81%). The product was recrystallized from ethyl acetate—hexane to afford colorless needles, m.p.109°–110° C.

Reference Example 8

Sodium hydride (60% in oil, 2.0 g) was added, in small portions at 0° C. a solution of diethyl cyanomethylphosphonate (8.2 g) in tetrahydrofuran (150 ml). The mixture was stirred for about 15 minutes, to which was added 4-[2-(5-methyl-2-phenyl-4-oxazolyl)ethoxy]benzaldehyde (13.0 g), and the mixture was stirred for 30 minutes at room temperature. The reaction mixture was poured into ice-water, which was subjected to extraction with ethyl acetate. The ethyl acetate layer was washed with water and dried (MgSO$_4$), then the solvent was distilled off to leave 4-[2-(5-methyl-2-phenyl-4-oxazolyl)ethoxy]cinnamonitrile (11.8 g, 85%). The product was recrystallized from ethyl acetate—hexane to give colorless needles, m.p.112°–113° C.

Reference Examples 9 to 15

In substantially the same manner as in Reference Example 8, compounds shown in [Table 2] were obtained.

TABLE 2

A—(CH$_2$)$_n$—O—⟨benzene ring⟩—CH=CHCN (E)

| Reference Example No. | A | n | Yield (%) | Melting point (°C.) | Recrystallization Solvent |
|---|---|---|---|---|---|
| 9 | 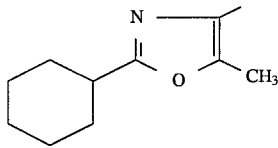 | 2 | 79 | Note 1) oily product | — |
| 10 | 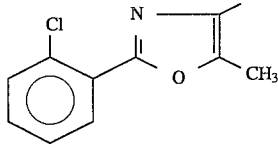 | 2 | 67 | 121–122 | ethyl acetate-hexane |

TABLE 2-continued $$A-(CH_2)_n-O-\underset{CH=CHCN}{\underset{(E)}{C_6H_4}}$$

| Reference Example No. | A | n | Yield (%) | Melting point (°C.) | Recrystallization Solvent |
|---|---|---|---|---|---|
| 11 | 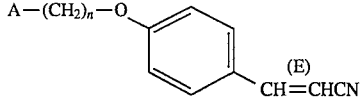 | 2 | 98 | 97–98 | dichloromethane-isopropyl ether |
| 12 | 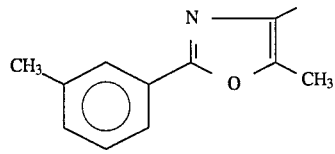 | 2 | 48 | 147–148 | dichloromethane-isopropyl ether |
| 13 | 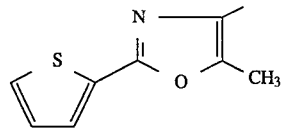 | 1 | Note 2) — | | |
| 14 | 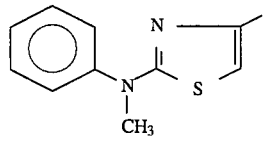 | 2 | 87 | Note 3) oily product | — |
| 15 | 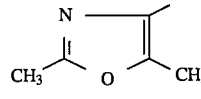 | 1 | 76 | 97–98 | ethyl acetate-hexane |

Note 1) Mixture of (E)- and (Z)-compound in a ratio of 3:1.
NMR(δ ppm in CDCl$_3$): 1.2–2.1(10H, m), 2.24(3H, s), 2.6–2.8(1H, m), 2.89(2H, t, J=7Hz), 5.28(d, J=12Hz) and 5.70(d, J=16.5Hz)(total 1H), 6.88 and 6.91(total 2H, each d, J=9Hz), 7.02(d, J=12Hz) and 7.32(d, J=16.5Hz)(total 1H), 7.37 and 7.76(total 2H, each d, J=9Hz)
Note 2) Used for the subsequent reaction without isolation
Note 3) Mixture of (E)- and (Z)-compound in a ratio of 5:2
NMR(δ ppm) in CDCl$_3$): 2.24(3H, s), 2.38(3H, s), 2.88(2H, t, J=7Hz), 4.21 and 4.23(t, J=7Hz)(total 2H), 5.28(d, J=12Hz) and 5.71(d, J=16.5Hz)(total 1H), 6.89 and 6.93(total 2H, each d, J=9Hz), 7.02(d, J=12Hz) and 7.32(d, J=16.5Hz)(total 1H), 7.37 and 7.77(total 2H, each d, J=9Hz).

Reference Example 16

A mixture of 4-[2-(5-methyl-2-phenyl-4-oxazolyl)ethoxy]cinnamonitrile (4.0 g), palladium-carbon (5%, 0.5 g) and ethyl acetate (50 ml) was subjected to catalytic hydrogenation at room temperature under 1 atmospheric pressure. The catalyst was filtered off, then the filtrate was concentrated under reduced pressure to leave 3-[4-[2-(5-methyl-2-phenyl-4-oxazolyl)ethoxy]phenyl]propionitrile (3.7 g, 93%). The product was recrystallized from ethyl acetate—hexane to give colorless needles, m.p.109°–110° C.

Reference Examples 17 to 21

In substantially the same manner as in Reference Example 16, compounds shown in [Table 3] were obtained.

TABLE 3

A—(CH₂)ₙO—⟨phenyl⟩—Y—CN

| Reference Example No. | A | n | Y | Yield (%) | Melting point (°C.) | Recrystallization Solvent |
|---|---|---|---|---|---|---|
| 17 | 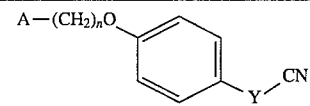 | 2 | —CH₂CH₂— | 79 | Note 1) oily product | — |
| 18 | 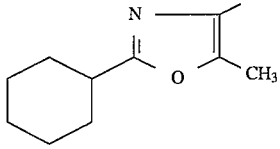 | 2 | —CH₂CH₂— | 77 | 116–117 | dichloromethane-isopropyl ether |
| 19 | 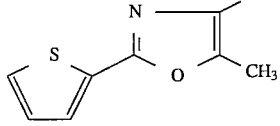 | 2 | —CH₂CH₂— | 93 | 79–80 | ethyl ether-hexane |
| 20 | 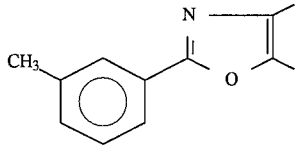 | 1 | —CH₂CH₂— | Note 2) 54 | Note 3) oily product | — |
| 21 | 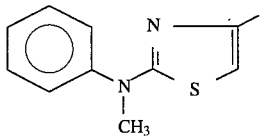 | 2 | —CH₂CH₂— | quant. | 62–63 | acetone-hexane |

Note 1) NMR(δ ppm in CDCl₃): 1.2–2.1(10H, m), 2.24(3H, s), 2.57(2H, t, J=7.5Hz), 2.69(1H, tt, J=11.5, 3.5Hz), 2.87(2H, t, J=7Hz), 2.89(2H, t, J=7.5Hz), 4.14(2H, t, J=7Hz), 6.84(2H, d, J=8Hz), 7.12(2H, d, J=8.5Hz)
Note 2) Overall yield from the corresponding benzaldehyde
Note 3) NMR(δ ppm in CDCl₃): 2.59(2H, t, J=7Hz), 2.91(2H, t, J=7Hz), 3.55(3H, s), 5.00(2H, d, J=1Hz), 6.46(1H, t, J=1Hz), 6.97(2H, d, J=8.5Hz), 7.15(2H, d, J=8.5Hz), 7.2–7.5(5H, m).

Reference Example 22

Sodium hydride (60% in oil, 2.2 g) was added, in small portions at 0° C., to a solution of triethyl phosphonoacetate (11.2 g) in tetrahydrofuran (200 ml), and the mixture was stirred for 15 minutes at the same temperature. To the mixture was then added 4-[2-(5-methyl-2-phenyl-4-oxazolyl)ethoxy]benzaldehyde (14.0 g), which was stirred for one hour at room temperature. The reaction mixture was poured into ice-water, which was neutralized with 2N HCl. Resulting crystalline precipitate was collected by filtration, which was recrystallized from ethyl acetate—hexane to give ethyl 4-[2-(5-methyl-2-phenyl-4-oxazolyl)ethoxy]cinnamate (15.1 g, 88%). Colorless needles, m.p.114°–115° C.

Reference Example 23

A toluene solution of diisobutylaluminum hydride (1.5M, 67 ml) was added dropwise at 0° C. to a suspension of ethyl 4-[2-(5-methyl-2-phenyl-4-oxazolyl)ethoxy]cinnamate (15.0 g) in toluene (200 ml). The mixture was stirred for 2 hours at room temperature, to which was added 2N HCl (200 ml) under ice-cooling. The organic layer was washed with water, dried (MgSO₄) and concentrated to give (E)-3-[4-[2-(5-methyl-2-phenyl-4-oxazolyl)ethoxy]phenyl]-2-propen-1-ol (12,0 g, 90%), which was recrystallized from ethyl acetate to give colorless prisms, m.p.127°–128° C.

Reference Example 24

A mixture of (E)-3-[4-[2-(5-methyl-2-phenyl-4-oxazolyl)ethoxy]phenyl]-2-propen-1-ol (3.1 g), palladium-carbon (5%, 0.5 g) and ethyl acetate (50 ml) was subjected to catalytic hydrogenation under 1 atmospheric pressure at room temperature. The catalyst was filtered off, and the filtrate was concentrated under reduced pressure to yield 3-[4-[2-(5-methyl-2-phenyl-4-oxazolyl)ethoxy]phenyl]propan-1-ol (2.8 g, 90%), which was recrystallized from ethyl acetate—hexane to give colorless needles, m.p.99°–100° C.

Reference Example 25

To a mixture of 3-[4-[2-(5-methyl-2-phenyl-4-oxazolyl)ethoxy]phenyl]propan-1-ol (2.6 g) and benzene (50 ml) was added phosphorus tribromide (PBr₃) (2.1 g), which was stirred for 2 hours at 70° C. The reaction mixture was poured into water, which was subjected to extraction with ethyl acetate. The ethyl acetate layer was washed with water and dried (MgSO₄), then the solvent was distilled off to leave 3-[4-[2-(5-methyl-2-phenyl-4-oxazolyl)ethoxy]phenyl]propyl bromide (0.98 g, 32%), which was recrystallized from ethyl acetate—hexane to give colorless needles, m.p.78°–79° C.

Reference Example 26

To a mixture of 5-amino-2-[2-(5-methyl-2-phenyl-4-oxazolyl)ethoxy]pyridine (9.1 g), an aqueous solution of HBr (47%, 14.2 ml) and acetone (150 ml) was added dropwise, at temperature not exceeding 10° C. a solution of sodium nitrite ($NaNO_2$) (2.33 g) in water (10 ml). The mixture was stirred for 30 minutes at 10° C., to which was added acrylonitrile ($CH_2$=CHCN) (12.1 ml). To the mixture was added, while stirring vigorously, copper(I) oxide ($Cu_2O$) (0.1 g). The reaction mixture was stirred for further one hour at temperature ranging from 30° to 35° C., followed by concentration under reduced pressure. The concentrate was poured into water, which was made alkaline with a conc. ammonia water, followed by extraction with ethyl acetate. The ethyl acetate layer was washed with water and dried ($MgSO_4$), then the solvent was distilled off under reduced pressure. The residual oily product was subjected to a silica gel column chromatography. From the fractions eluted with ethyl acetate—hexane (1:1, v/v), was obtained 2-bromo-3-[2-[2-(5-methyl-2-phenyl-4-oxazolyl)ethoxy]-5-pyridyl]propionitrile (6.11 g, 48%), which was recrystallized from ethyl acetate—hexane to give colorless crystals, m.p.93°–94° C.

Reference Example 27

A mixture of 2-bromo-3-[2-[2-(5-methyl-2-phenyl-4-oxazolyl)ethoxy]-5-pyridyl]propionitrile (2.0 g), palladium-carbon (5%, 0.2 g) and dioxane (30 ml) was subjected to catalytic reduction under 1 atmospheric pressure at room temperature. The catalyst was filtered off, then the filtrate was concentrated under reduced pressure. The concentrate was subjected to a silica gel column chromatography. From the fractions eluted with ethyl acetate—hexane (2:3, v/v), was obtained 3-[2-[2-(5-methyl-2-phenyl-4-oxazolyl)ethoxy]-5-pyridyl]propionitrile (1.3 g, 78%), which was recrystallized from ethyl acetate—hexane to give colorless crystals, m.p.105°–106° C.

Reference Example 28

A mixture of 2-bromo-3-[2-[2-(5-methyl-2-phenyl-4-oxazolyl)ethoxy]-5-pyridyl]propionitrile (4.5 g), lithium bromide (LiBr) (1.14 g), lithium carbonate ($Li_2CO_3$) (2.17 g) and N,N-dimethylformamide (50 ml) was stirred for 2.5 hours at 120° C. The reaction mixture was poured into water, which was subjected to extraction with ethyl acetate. The ethyl acetate layer was washed with water and dried ($MgSO_4$), then the solvent was distilled off under reduced pressure to leave (E)-3-[2-[2-(5-methyl-2-phenyl-4-oxazolyl)ethoxy]-5-pyridyl]acrylonitrile (3.2, 89%), which was recrystallized from ethyl acetate—hexane to give pale yellow crystals, m.p.116°–117° C.

Reference Example 29

A mixture of 4-[2-[2-(2-chlorophenyl)-5-methyl-4-oxazolyl]ethoxy]benzaldehyde (2.0 g), ethyl cyanoacetate (0.795 g), piperidine (0.15 g) and pyridine (30 ml) was stirred for 2 hours at 100°–110° C. The reaction mixture was poured into water. Resulting crystalline precipitate was collected by filtration and recrystallized from dichloromethane-ethanol to give ethyl 4-[2-[2-(2-chlorophenyl)-5-methyl-4-oxazolyl]ethoxy]-α-cyanocinnamate (2.45 g, 96%) as colorless needles, m.p.120°–121° C.

Reference Example 30

To a mixture of ethyl 4-[2-[2-(2-chlorophenyl)-5-methyl-4-oxazolyl]ethoxy]-α-cyanocinnamate (2.25 g) and dioxane (30 ml)—ethanol (30 ml) was added sodium borohydride (0.06 g) under ice-cooling. The mixture was stirred for one hour at the same temperature. The reaction mixture was poured into ice-water, which was made acid and subjected to extraction with ethyl acetate. The ethyl acetate layer was washed with water and dried ($MgSO_4$), then the solvent was distilled off under reduced pressure. The residue was subjected to a silica gel column chromatography. From the fractions eluted with chloroform-methanol (50:1, v/v), was obtained ethyl 3-[4-[2-[2-(2-chlorophenyl)-5-methyl-4-oxazolyl]ethoxy]phenyl]-2-cyanopropionate (2.25 g, quant.) as an oily product. NMR(δ ppm in $CDCl_3$): 1.27(3H,t,J=7Hz), 2.39(3H,s), 3.00(2H,t,J=6.5Hz), 3.12(1H,dd,J=14&8Hz), 3.22(1H,dd,J=14&6Hz), 3.66(1H,dd,J=8&6Hz), 4.22(2H,q, J=7Hz), 4.24(2H,t,J=6.5Hz), 6.87(2H,d,J=9Hz), 7.17(2H,d, J=9Hz), 7.25–7.5(3H,m), 7.85–8.0(1H,m).

Reference Example 31

A mixture of ethyl 3-[4-[2-[2-(2-chlorophenyl)-5-methyl-4-oxazolyl]ethoxy]phenyl]-2-cyanopropionate (2.24 g), 1N NaOH (15 ml) and ethanol (50 ml) was stirred for one hour at room temperature. The reaction mixture was poured into water and made acidic, which was subjected to extraction with ethyl acetate. The ethyl acetate layer was washed with water and dried ($MgSO_4$), then the solvent was distilled off under reduced pressure to leave a crystalline product, which was added to pyridine (5 ml)—o-dichlorobenzene (50 ml), and the mixture was heated for 2 hours under reflux. The reaction mixture was concentrated under reduced pressure, which was subjected to a silica gel column chromatography. From the fractions eluted with chloroform was obtained 3-[4-[2-[2-(2-chlorophenyl)-5-methyl-4-oxazolyl]ethoxy]phenyl]propionitrile (1.5 g, 80%), which was recrystallized from dichloromethane—isopropyl ether to give pale yellow crystals, m.p.88°–89° C.

Reference Example 32

In substantially the same manner as in Reference Example 22, was obtained ethyl 4-(5-methyl-2-phenyl-4-oxazolylmethoxy)cinnamate, which was recrystallized from ethyl acetate—hexane to give colorless prisms, m.p.145°–146° C.

Reference Example 33

In substantially the same manner as in Reference Example 23, was obtained (E)-3-[4-(5-methyl-2-phenyl-4-oxazolylmethoxy)phenyl]-2-propen-1-ol, which was recrystallized from ethyl acetate—hexane to give colorless prisms, m.p.134°–135° C.

Reference Example 34

Activated manganese dioxide ($MnO_2$) (9.0 g) was added to a solution of (E)-3-[4-(5-methyl-2-phenyl-4-oxazolylmethoxy)phenyl]-2-propen-1-ol (3.7 g) in dichloromethane (80 ml), which was stirred for one hour at room temperature. The reaction mixture was subjected to filtration through celite layer. The filtrate was concentrated under reduced pressure to give 4-(5-methyl-2-phenyl-4-oxazolylmethoxy)cinnamoaldehyde (2.6 g, 70%), which was recrystallized from ethyl acetate—hexane to yield colorless prisms, m.p.114°–115° C.

Reference Example 35

Sodium hydride (60% in oil, 0.32 g) was added, in small portions at 0° C., to a solution of diethyl cyanomethylphosphonate (1.3 g) in tetrahydrofuran (50 ml). The mixture was stirred for 15 minutes at the same temperature, to which was then added 4-(5-methyl-2-phenyl-4-oxazolylmethoxy)cinnamoaldehyde (2.0 g), followed by stirring for 30 minutes under ice-cooling. The reaction mixture was poured into water, which was subjected to extraction with ethyl acetate. The ethyl acetate layer was washed with water and dried ($MgSO_4$), which was then concentrated to give (E,E)-5-[4-(5-methyl-2-phenyl-4-oxazolylmethoxy)phenyl]-2,4-pentadienenitrile (1.5 g, 68%). Recrystallization of the product from ethyl acetate—hexane afforded colorless needles, m.p.120°–121° C.

Reference Example 36

In substantially the same manner as in Reference Example 24, was obtained 3-[4-(5-methyl-2-phenyl-4-oxazolylmethoxy)phenyl]propan-1-ol, which was recrystallized from ethyl acetate—hexane to yield colorless prisms, m.p.72°–73° C.

Reference Example 37

In substantially the same manner as in Reference 25, was obtained 3-[4-(5-methyl-2-phenyl-4-oxazolylmethoxy)phenyl]propyl bromide, which was recrystallized from ethyl ether—hexane to yield colorless prisms, m.p.80°–81° C.

Reference Example 38

A mixture of 3-[4-(5-methyl-2-phenyl-4-oxazolylmethoxy)phenyl]propyl bromide (1.5 g), powdered potassium cyanide (1.52 g) and N,N-dimethylformamide (30 ml) was stirred for 3 hours at 80° C. The reaction mixture was poured into water, which was subjected to extraction with ethyl acetate. The ethyl acetate layer was washed with water and dried (MgSO$_4$), which was then concentrated to give 4-[4-(5-methyl-2-phenyl-4-oxazolylmethoxy)phenyl]butyronitrile (1.2 g, 92%). Recrystallization of the product from ethyl acetate—hexane gave colorless needles, m.p.73°–74° C.

Reference Example 39

In substantially the same manner as in Reference Example 38, 4-[4-[2-(5-methyl-2-phenyl-4-oxazolyl]ethoxy]phenyl]butyronitrile, which was recrystallized from ethyl ether—hexane to yield colorless needles, m.p.69°–70° C.

Reference Example 40

According to the method described for Reference Example 22, 4-(5-methyl-2-phenyl-4-oxazolylmethoxy)cinnamoaldehyde was allowed to react with triethyl phosphonoacetate to give ethyl (E,E)-5-[4-(5-methyl-2-phenyl-4-oxazolylmethoxy)phenyl]-2, 4-pentadienoate, followed by recrystallization from ethyl acetate—hexane to give colorless prisms, m.p.137°–138° C.

Reference Example 41

According to the method described for Reference Example 16, ethyl (E,E)-5-[4-(5-methyl-2-phenyl-4-oxazolylmethoxy)phenyl]-2,4-pentadienoate was subjected to catalytic hydrogenation to give ethyl 5-[4-(5-methyl-2-phenyl-4-oxazolylmethoxy)phenyl]valerate. Recrystallization from hexane gave colorless rods, m.p.57°–58° C.

Reference Example 42

A solution of ethyl 5-[4-(5-methyl-2-phenyl-4-oxazolylmethoxy)phenyl]valerate (2.55 g) in ether (20 ml) was added dropwise, under ice-cooling, to a suspension of lithium aluminum hydride (LiAlH$_4$) (0.247 g) in ether (40 ml). The mixture was stirred for 15 minutes under ice-cooling, to which was added water (2 ml). Insoluble solid was filtered off, and the filtrate was concentrated to give 5-[4-(5-methyl-2-phenyl-4-oxazolylmethoxy)phenyl]-1-pentanol (2.15 g, 94%), which was recrystallized from ethyl acetate—hexane to give colorless rods, m.p.78°–79° C.

Reference Example 43

According to the method described for Reference Example 25, 5-[4-(5-methyl-2-phenyl-4-oxazolylmethoxy)phenyl]-1-pentanol was allowed to react with phosphorus tribromide to give 5-[4-(5-methyl-2-phenyl-4-oxazolylmethoxy)phenyl]pentyl bromide. Recrystallization from ether-hexane gave colorless needles, m.p.58°–59° C.

Reference Example 44

According to the method described for Reference Example 38, 5-[4-(5-methyl-2-phenyl-4-oxazolylmethoxy)phenyl]pentyl bromide was allowed to react with potassium cyanide to give 5-[4-(5-methyl-2-phenyl-4-oxazolylmethoxy)phenyl]hexanenitrile. Recrystallization from ether-hexane afforded colorless prisms, m.p.76°–77° C.

Reference Example 45

A mixture of 4-chloromethyl-5-methyl-2-phenyloxazole (9.2 g), p-hydroxyacetophenone (7.95 g), potassium carbonate (6.73 g) and N,N-dimethylformamide (DMF) (100 ml) was stirred for 2.5 hours at temperatures ranging from 70° to 80° C. The reaction mixture was poured into water and extracted with ethyl acetate. The ethyl acetate layer was washed with water, and dried (MgSO$_4$), then the solvent was distilled off to give 4'-(5-methyl-2-phenyl-4-oxazolylmethoxy)acetophenone (11.6 g, 85%). Recrystallization from ethyl acetate—ether gave colorless prisms, m.p.126°–127° C.

Reference Example 46

According to the method described for Reference Example 22, 4'-(5-methyl-2-phenyl-4-oxazolylmethoxy)acetophenone was allowed to react with trimethyl phosphonoacetate gave methyl (E)-3-[4-(5-methyl-2-phenyl-4-oxazolylmethoxy)phenyl]-2-butenoate. Recrystallization from ethyl acetate—hexane gave colorless prisms, m.p.125°–126° C.

Reference Example 47

According to the method described for Reference Example 23, methyl (E)-3-[4-(5-methyl-2-phenyl-4-oxazolylmethoxy)phenyl]-2-butenoate was subjected to reduction with diisobutylaluminum hydride to give (E)-3-[4-(5-methyl-2-phenyl-4-oxazolylmethoxy)phenyl]-2-buten-1-ol. Recrystallization from ethyl acetate—hexane gave colorless prisms, m.p.126°–127° C.

Reference Example 48

According to the method described for Reference Example 34, (E)-3-[4-(5-methyl-2-phenyl-4-oxazolylmethoxy)phenyl]-2-buten-1-ol was subjected to oxidation with activated manganese dioxide to give (E)-3-[4-(5-methyl-2-phenyl-4-oxazolylmethoxy)phenyl]-2-buten-1-al. Recrystallization from ethyl acetate—hexane gave colorless prisms, m.p.94°–95° C.

Reference Example 49

According to the method described for Reference Example 35, (E)-3-[4-(5-methyl-2-phenyl-4-oxazolylmethoxy)phenyl]-2-buten-1-al was allowed to react with diethyl cyanomethylphosphonate gave (E,E)-5-[4-(5-methyl-2-phenyl-4-oxazolylmethoxy)phenyl]-2,4-hexadienenitrile. Recrystallization from ethyl acetate—hexane gave colorless prisms, m.p.134°–136° C.

Reference Example 50

According to the method described for Reference Example 45, 4-chloromethyl-5-methyl-2-phenyloxazol was allowed to react with m-hydroxybenzaldehyde to give 3-(5-methyl-2-phenyl-4-oxazolylmethoxy)benzaldehyde. Recrystallization from ethanol gave colorless prisms, m.p.67°–68° C.

Reference Example 51

According to the method described for Reference Example 22, 3-(5-methyl-2-phenyl-4-oxazolylmethoxy)benzaldehyde was allowed to react with triethyl phosphonoacetate to give ethyl 3-(5-methyl-2-phenyl-4-oxazolylmethoxy)cinnamate. Recrystallization from ethanol gave colorless prisms, m.p.94°–95° C.

Reference Example 52

According to the method described for Reference Example 23, ethyl 3-(5-methyl-2-phenyl-4-oxazolylmethoxy)cinnamate was subjected to reduction with diisobutylaluminum hydride to give (E)-3-[3-(5-methyl-2-phenyl-4-oxazolylmethoxy)phenyl]-2-propen-1-ol. Recrystallization from ethyl acetate gave colorless prisms, m.p.120°–121° C.

Reference Example 53

According to the method described for Reference Example 34, (E)-3-[3-(5-methyl-2-phenyl-4-oxazolylmethoxy)phenyl]-2-propen-1-ol was subjected to oxidation with activated manganese dioxide to give (E)-3-[3-(5-methyl-2-phenyl-4-oxazolylmethoxy)phenyl]-2-propen-1-al. Recrystallization from ethyl acetate—hexane gave colorless prisms, m.p.103°–104° C.

Reference Example 54

According to the method described for Reference Example 35, (E)-3-[3-(5-methyl-2-phenyl-4-oxazolylmethoxy)phenyl]-2-propen-1-al was allowed to react with diethyl cyanomethylphosphonate to give (E,E)-5-[3-(5-methyl-2-phenyl-4-oxazolylmethoxy)phenyl]-2,4-pentadienenitrile as an oily product.

Reference Example 55

According to the method described for Reference Example 45, 2-chloromethyl-5-methyl-4-phenylthiazole was allowed to react with p-hydroxybenzaldehyde to give 4-(5-methyl-4-phenyl-2-thiazolylmethoxy)benzaldehyde. Recrystallization from ethyl acetate—isopropyl ether gave colorless prisms, m.p.81°–82° C.

Reference Example 56

According to the method described for Reference Example 22, 4-(5-methyl-4-phenyl-2-thiazolylmethoxy)benzaldehyde was allowed to react with trimethyl phosphonoacetate to give methyl 4-(5-methyl-4-phenyl-2-thiazolylmethoxy)cinnamate. Recrystallization from ethyl acetate—hexane gave colorless prisms, m.p.142°–143° C.

Reference Example 57

According to the method described for Reference Example 23, methyl 4-(5-methyl-4-phenyl-2-thiazolylmethoxy)cinnamate was subjected to reduction with diisobutylaluminum hydride to give (E)-3-[4-(5-methyl-4-phenyl-2-thiazolylmethoxy)phenyl]-2-propen-1-ol. Recrystallization from ethyl acetate—isopropyl ether gave colorless prisms, m.p.125°–126° C.

Reference Example 58

According to the method described for Reference Example 34, (E)-3-[4-(5-methyl-4-phenyl-2-thiazolylmethoxy)phenyl]-2-propen-1-ol was subjected to oxidation reaction with activated manganese dioxide to give (E)-3-[4-(5-methyl-4-phenyl-2-thiazolylmethoxy)phenyl]-2-propen-1-al. Recrystallization from ethyl acetate—hexane gave colorless prisms, m.p.116°–117° C.

Reference Example 59

According to the method described for Reference Example 35, (E)-3-[4-(5-methyl-4-phenyl-2-thiazolylmethoxy)phenyl]-2-propen-1-al was allowed to react with diethyl cyanomethylphosphonate to give (E,E)-5-[4-(5-methyl-4-phenyl-2-thiazolylmethoxy)phenyl]-2,4-pentadienenitrile. Recrystallization from ethyl acetate—ether gave colorless prisms, m.p.108°–109° C.

Reference Example 60

According to the method described for Reference Example 45, 2-chloromethyl-5-methyl-4-phenyloxazole was allowed to react with p-hydroxybenzaldehyde to give 4-(5-methyl-4-phenyl-2-oxazolylmethoxy)benzaldehyde. Recrystallization from ethyl acetate—isopropyl ether gave colorless prisms, m.p.90°–91° C.

Reference Example 61

According to the method described for Reference Example 22, 4-(5-methyl-4-phenyl-2-oxazolylmethoxy)benzaldehyde was allowed to react with trimethyl phosphonoacetate to give methyl 4-(5-methyl-4-phenyl-2-oxazolylmethoxy)cinnamate. Recrystallization from ethyl acetate—isopropyl ether gave colorless prisms, m.p.109°–110° C.

Reference Example 62

According to the method described for Reference Example 23, methyl 4-(5-methyl-4-phenyl-2-oxazolylmethoxy)cinnamate was subjected to reduction with diisobutylaluminum hydride to give (E)-3-[4-(5-methyl-4-phenyl-2-oxazolylmethoxy)phenyl]-2-propen-1-ol. Recrystallization from chloroform-isopropyl ether gave colorless prisms, m.p.154°–155° C.

Reference Example 63

According to the method described for Reference Example 34, (E)-3-[4-(5-methyl-4-phenyl-2-oxazolylmethoxy)phenyl]-2-propen-1-ol was subjected to oxidation with activated manganese dioxide to give (E)-3-[4-(5-methyl-4-phenyl-2-oxazolylmethoxy)phenyl]-2-propen-1-al. Recrystallization from chloroform ether gave colorless prisms, m.p.144°–146° C.

Reference Example 64

According to the method described for Reference Example 35, (E)-3-[4-(5-methyl-4-phenyl-2-oxazolylmethoxy)phenyl]-2-propen-1-al was allowed to react with diethyl cyanomethylphosphonate to give (E,E)-5-[4-(5-methyl-4-phenyl-2-oxazolylmethoxy)phenyl]-2,4-pentadienenitrile. Then, according to the method described for Reference Example 16, (E,E)-5-[4-(5-methyl-4-phenyl-2-oxazolylmethoxy)phenyl]-2,4-pentadienenitrile was subjected to catalytic reduction to give 5-[4-(5-methyl-4-phenyl-2-oxazolylmethoxy)phenyl]valeronitrile. Recrystallization from ethyl acetate—ether—hexane gave colorless prisms, m.p.65°–66° C.

Reference Example 65

According to the method described for Reference Example 45, 4-chloromethyl-5-methyl-2-(2-naphthyl)oxazole was allowed to react with p-hydroxybenzaldehyde to give 4-[5-methyl-2-(2-naphthyl)-4-oxazolylmethoxy]benzaldehyde. Recrystallization from chloroform-ether gave colorless prisms, m.p.163°–164° C.

Reference Example 66

According to the method described for Reference Example 22, 4-[5-methyl-2-(2-naphthyl)-4-oxazolylmethoxy]benzaldehyde was allowed to react with trimethyl phosphonoacetate to give methyl 4-[5-methyl-2-(2-naphthyl)-4-oxazolylmethoxy]cinnamate. Recrystallization from chloroform-ether gave colorless prisms, m.p.185°–186° C.

Reference Example 67

According to the method described for Reference Example 23, methyl 4-[5-methyl-2-(2-naphthyl)-4-oxazolylmethoxy]cinnamate was subjected to reduction with diisobutylaluminum hydride to give (E)-3-[4-[5-methyl-2-(2-naphthyl)-4-oxazolylmethoxy]phenyl]-2-propen-1-ol. Recrystallization from chloroform-ether gave colorless prisms, m.p.159°–160° C.

Reference Example 68

According to the method described for Reference Example 34, (E)-3-[4-[5-methyl-2-(2-naphthyl)-4-oxazolylmethoxy]phenyl]-2-propen-1-ol was subjected to oxidation with activated manganese dioxide to give (E)-3-[4-[5-methyl-2-(2-naphthyl)-4-oxazolylmethoxy]phenyl]-2-propen-1-al. Recrystallization from chloroform-ether gave colorless prisms, m.p.179°–180° C.

Reference Example 69

According to the method described for Reference Example 35, (E)-3-[4-[5-methyl-2-(2-naphthyl)-4-oxazolylmethoxy]phenyl]-2-propen-1-al was allowed to react with diethyl cyanomethylphosphonate to give (E,E)-5-[4-[5-methyl-2-(2-naphthyl)-4-oxazolylmethoxy]phenyl]-2,4-pentadienenitrile. Recrystallization from ethyl acetate—ether gave colorless prisms, m.p.159°–160° C.

Reference Example 70

According to the method described for Reference Example 45, 4-chloromethyl-5-methyl-2-(2-naphthyl)oxazole was allowed to react with 4-(4-hydroxyphenyl)butyronitrile to give 4-[4-[5-methyl-2-(2-naphthyl)-4-oxazolylmethoxy]phenyl]butyronitrile. Recrystallization from chloroform-ether gave colorless prisms, m.p.149°–151° C.

Reference Example 71

According to the method described for Reference Example 45, 4-chloromethyl-5-methyl-3-(2-naphthyl)oxazole was allowed to react with methyl 5-(4-hydroxyphenyl)valerate to give methyl 5-[4-[5-methyl-2-(2-naphthyl)-4-oxazolylmethoxy]phenyl]valerate. Then, according to the method described for Reference Example 42, methyl 5-[4-[5-methyl-2-(2-naphthyl)-4-oxazolylmethoxy]phenyl]valerate was subjected to reduction with lithium aluminum hydride to give 5-[4-[5-methyl-2-(2-naphthyl)-4-oxazolylmethoxy]phenyl]pentan-1-ol. Recrystallization from ethyl acetate—ether gave colorless needles, m.p.128°–129° C.

Reference Example 72

To a mixture of 5-[4-[5-methyl-2-(2-naphthyl)-4-oxazolylmethoxy]phenyl]pentan-1-ol (1.1 g), triethylamine (0.333 g) and dichloromethane (40 ml) was added dropwise, under ice-cooling, methanesulfonyl chloride (0.345 g). The mixture was stirred for 2 hours at room temperature, which was washed with water and dried (MgSO$_4$). The solvent was distilled off to leave 5-[4-[5-methyl-2-(2-naphthyl)-4-oxazolylmethoxy]phenyl]pentyl methanesulfonate (1.21 g, 92%). Recrystallization from dichloromethane-ether gave colorless prisms, m.p.132°–133° C.

Reference Example 73

According to the method described for Reference Example 38, 5-[4-[5-methyl-2-(2-naphthyl)-4-oxazolylmethoxy]phenyl]pentyl methanesulfonate was allowed to react with potassium cyanide to give 6-[4-[5-methyl-2-(2-naphthyl)-4-oxazolylmethoxy]phenyl]hexanenitrile. Recrystallization from ethyl acetate—isopropyl ether gave colorless prisms, m.p.116°–117° C.

Reference Example 74

According to the method described for Reference Example 35, 4-[3-(5-methyl-2-phenyl-4-oxazolyl)propoxy]benzaldehyde was allowed to react with diethyl cyanomethylphosphonate to give 4-[3-(5-methyl-2-phenyl-4-oxazolyl)-propoxy]cinnamonitrile. Recrystallization from ethyl acetate—isopropyl ether—hexane gave colorless prisms, m.p.97°–98° C.

Reference Example 75

According to the method described for Reference Example 45, 2-chloromethyl-5-methyl-4-phenyloxazole was allowed to o-hydroxybenzaldehyde to give 2-(5-methyl-4-phenyl-2-oxazolylmethoxy)benzaldehyde. Recrystallization from ethyl acetate—ether gave colorless prisms, m.p.95°–96° C.

Reference Example 76

According to the method described for Reference Example 22, 2-(5-methyl-4-phenyl-2-oxazolylmethoxy)benzaldehyde was allowed to react with trimethyl phosphonoacetate to give methyl 2-(5-methyl-4-phenyl-2-oxazolylmethoxy)cinnamate. Recrystallization from ethyl acetate—chloroform-ether gave colorless prisms, m.p.128°–129° C.

Reference Example 77

According to the method described for Reference Example 23, methyl 2-(5-methyl-4-phenyl-2-oxazolylmethoxy)cinnamate was subjected to reduction with diisobutylaluminum hydride to give (E)-3-[2-(5-methyl-4-phenyl-2-oxazolylmethoxy)phenyl]-2-propen-1-ol. Recrystallization from ethyl acetate-ether gave colorless prisms, m.p.128°–129° C.

Reference Example 78

According to the method described for Reference Example 34, (E)-3-[2-(5-methyl-4-phenyl-2-oxazolylmethoxy)phenyl]-2-propen-1-ol was subjected to oxidation with activated manganese dioxide to give (E)-3-[2-(5-methyl-4-phenyl-2-oxazolylmethoxy)phenyl]-2-propen-1-al. Recrystallization from chloroform—isopropyl ether gave colorless prisms, m.p.112°–113° C.

Reference Example 79

According to the method described for Reference Example 35, (E)-3-[2-(5-methyl-4-phenyl-2-oxazolylmethoxy)phenyl]-2-propen-1-al was allowed to react with diethyl cyanomethylphosphonate to give (E,E)-5-[2-(5-methyl-4-phenyl-2-oxazolylmethoxy)phenyl]-2,4-pentadienenitrile. Recrystallization from ethanol-chloroform gave colorless prisms, m.p.128°–129° C.

Reference Example 80

According to the method described for Reference Example 45, 2-(benzo[b]furan-2-yl)-4-chloromethyl-5-methyloxazole was allowed to react with 4-(4-hydroxyphenyl)butyronitrile to give 4-[4-[2-(benzo[b]furan-2-yl)-5-methyl-4-oxazolylmethoxy]phenyl]butyronitrile. Recrystallization from dichloromethane—isopropyl ether gave colorless prisms, m.p.118°–119° C.

Reference Example 81

According to the method described for Reference Example 45, 4-chloromethyl-2-(furan-2-yl)-5-methyloxazole was allowed to react with 4-(4hydroxyphenyl)butyronitrile to give 4-[4-[2-(furan-2yl)-5-methyl-4-oxazolylmethoxy]phenyl]butyronitrile as an oily product. NMR(δ ppm in CDCl$_3$): 1.85–2.05(2H,m), 2.31(2H,t,J=7Hz), 2.42(3H,s), 2.72(2H,t,J=7.5Hz), 4.97(2H,s), 6.52(1H,dd,J= 3.5&2Hz), 6.9–7.0(3H,m), 7.10(2H,d,J=9Hz), 7.53(1H,dd, J=2&1Hz).

Reference Example 82

According to the method described for Reference Example 45, 3-chloromethyl-1-methyl-5-phenyl-1,2,4-triazole was allowed to react with 4-(4-hydroxyphenyl)butyronitrile to give 4-[4-(1-methyl-5-phenyl-1,2,4-triazol-3-yl-methoxy)phenyl]butyronitrile. Recrystallization from dichloromethane-isopropyl ether gave colorless prisms, m.p.106°–107° C.

Reference Examples 83

In substantially the same manner as in Reference Example 1, 2-(5-methyl-2-phenyl-4-oxazolylmethoxy)-5-nitropyridine was obtained by reacting 2-chloro-5-nitropyridine with 5-methyl-2-phenyl-4-oxazolylmethanol. The yield was 84%. Recrystallization from dichloromethane-isopropyl ether gave pale yellow prisms, m.p. 142°–143° C.

Reference Example 84

In substantially the same manner as in Reference Example 2, 5-amino-2-(5-methyl-2-phenyl-4-oxazolylmethoxy)pyridine was obtained by subjecting 2-(5-methyl-2-phenyl-4-oxazolylmethoxy)-5-nitropyridine to catalytic hydrogenation. The yield was 81%. Recrystallization from methanol-isopropyl ether gave colorless prisms, m.p. 106°–107° C.

Reference Example 85

To a mixture of 5-amino-2-(5-methyl-2-phenyl-4-oxazolylmethoxy)pyridine (4.00 g), 47% HBr (12.2 g) and acetone (80 ml) was added dropwise a solution of sodium nitrite (NaNO$_2$) (1.08 g) in water (2 ml) at temperatures below 5° C. After stirring for 30 minutes, methyl acrylate (6.12 g) was added to the mixture, and then copper (I) oxide (0.20 g) was added at 10°–20° C. The mixture was stirred for further one hour at room temperature, followed by concentration under reduced pressure. The concentrate was diluted with conc. ammonia solution and extracted with ethyl acetate. The ethyl acetate layer was washed with water and dried (MgSO$_4$), then the solvent was distilled off under reduced pressure. The residual oily product was subjected to a silica gel chromatography. From the fractions eluted with ethyl acetate-hexane (1:5, v/v) was obtained 2-bromo-3-[2-(5-methyl-2-phenyl-4-oxazolylmethoxy)-5-pyridyl]propionate (2.27 g, 37%) as an oily substance. NMR(δ ppm in CDCl₃): 2.48(3H,s), 3.18(1H,dd,J=14.5&7Hz), 3.39(1H,dd, J=14.5&8Hz), 3.76(3H,s), 4.34(1H,dd,J=8&7Hz), 5.28(2Hs), 6.78(1H,d,J=8.5Hz), 7.35–7.5(4H,m), 7.95–8.1(3H,m).

Reference Example 86

A mixture of 2-bromo-3-[2-(5-methyl-2-phenyl-4-oxazolyl-methoxy)-5-pyridyl]propionate (4.00 g), 1,8-diazabicyclo[5,4,0]-7-undecene (1.41 g) and toluene (80 ml) was stirred 2 hours at 90°–100° C. The reaction mixture was poured into water and extracted with ethyl acetate. The ethyl acetate layer was washed with water and dried (MgSO₄), then the solvent was distilled off under reduced pressure. The residual oily product was subjected to a silica gel chromatography. From the fractions eluted with ethyl acetate-hexane (1:3, v/v) was obtained methyl (E)-3-[2-(5-methyl-2-phenyl-4-oxazolylmethoxy)-5-pyridyl]acrylate (2.71 g, 83%). Recrystallization from diethyl ether-isopropyl ether gave colorless prisms, m.p. 116°–117° C.

Reference Example 87

In substantially the same manner as in Reference Example 23, (E)-3-[2-(5-methyl-2-phenyl-4-oxazolylmethoxy)-5-pyridyl-2-pyridyl-2-propen-1-ol was obtained by reduction of methyl (E)-3-[2-(5-methyl-2-phenyl-4-oxazolylmethoxy)-5-pyridyl]acrylate with diisobutylalminium hydride. The yield was 76%. Recrystallization from dichloromethane-isopropyl ether gave colorless prisms, m.p. 116°–117° C.

Reference Example 88

In substantially the same manner as in Reference Example 34, (E)-3-[2-(5-methyl-2-phenyl-4- oxazolylmethoxy)-5-pyridyl-2-propen-1-al was obtained by oxidation of (E)-3-[2-(5-methyl-2-phenyl-4-oxazolylmethoxy)-5-pyridyl]-2-propen-1-ol with manganese dioxide. The yield was 92%. Recrystallization from dichloromethane-isopropyl ether gave colorless prisms, m.p. 147°–148° C.

Reference Example 89

In substantially the same manner as in Reference Example 24, 3-[2-(5-methyl-2-phenyl-4-oxazolylmethoxy)-5-pyridyl]propanol was obtained by subjecting (E)-3-[2-(5-methyl-2-phenyl-4-oxazolylmethoxy)-5-pyridyl]-2-propen-1-ol to catalytic hydrogenation. The yield was 82%. Recrystallization from diethyl ether-isopropyl ether gave colorless needles, m.p. 89°–90° C.

Reference Example 90

In substantially the same manner as in Reference Example 72, 3-[2-(5-methyl-2-phenyl-4-oxazolylmethoxy)pyridyl]propyl methanesulfonate was obtained as an oily product by methanesulfonylation of 3-[2-(5-methyl-2-phenyl-4-oxazolylmethoxy)-5-pyridyl]propanol. The yield was 89%. NMR(δ ppm in CDCl₃): 1.95–2.15(2H,m), 2.48(3H,s), 2.70(2H,t,J=7.5Hz), 3.01(3H,s), 4.24(2H,t,J=6.5Hz), 5.28(2H,s), 6.78(1H,d,J=8.5Hz), 7.35–7.5(4H,m), 7.95–8.1(3H,m).

Reference Example 91

In substantially the same manner as in Reference Example 38, 4-[2-(5-methyl-2-phenyl-4-oxazolylmethoxy)-5-pyridyl]butyronitrile was obtained as an oily product by reacting 3-[2-(5-methyl-2-phenyl-4-oxazolylmethoxy)-5-pyridyl]propyl methanesulfonate with potassium cyanide. The yield was 95%. NMR(δ ppm in CDCl₃): 1.85–2.05(2H,m), 2.35(2H,t,J=7Hz), 2.48(3H,s), 2.73(2H,t,J=7.5Hz), 5.28(2H, s), 6.80(1H,d,J=8.5Hz), 7.35–7.5(4H,m), 7.95–8.1(3H,m).

Reference Example 92

In substantially the same manner as in Reference Example 64, 5-[2-(5-methyl-2-phenyl-4-oxazolylmethoxy)-5-pyridyl]valeronitrile was obtained as an oily product by reacting (E)-3-[2-(5-methyl-2-phenyl-4-oxazolylmethoxy)-5-pyridyl]-2-propen-1-al with diethyl cyanomethylphosphonate, followed by catalytic hydrogenation. The yield was 96%. NMR(δ ppm in CDCl₃): 1.55–1.85(4H,m), 2.37(2H,t,J= 6.5Hz), 2.48(3H,s), 2.59(2H,t,J=7.5Hz), 5.27(2H,s), 6.77(1H,d,J=8.5Hz), 7.35–7.5(4H,m), 7.95–8.1(3H,m).

EXAMPLE 1

A mixture of 3-[4-[2-(5-methyl-2-phenyl-4-oxazolyl)ethoxy]phenyl]propionitrile (0.7 g), sodium azide (0.411 g), ammonium chloride (0.337 g) and N,N-dimethylformamide (15 ml) was stirred for 24 hours at 120° C. The reaction mixture was poured into water, which was subjected to extraction with ethyl acetate. The ethyl acetate layer was washed with water and dried, then the solvent was distilled off to leave 5-[2-[4-[2-(5-methyl-2-phenyl-4-oxazolyl)ethoxy]phenyl]ethyl]tetrazole (0.38 g, 48%), which was recrystallized from ethyl acetate—hexane to give colorless prisms, m.p.143°–144° C.

EXAMPLES 2 to 14

In substantially the same manner as in Example 1, compounds shown in [Table 4] and [Table 5] were obtained.

TABLE 4

$$A-(CH_2)_n-O-\underset{Y}{\overset{X}{\text{(pyridine)}}}-\underset{H}{\overset{N-N}{\underset{N}{\text{(tetrazole)}}}}$$

| Example No. | A | n | X | Y | Yield (%) | Melting point (°C.) | Recrystallization Solvent |
|---|---|---|---|---|---|---|---|
| 2 | phenyl-C(=N-)-O-C(CH₃)= | 2 | N | —CH₂CH₂— | 44 | 143–144 | ethanol |
| 3 | phenyl-C(=N-)-O-C(CH₃)= | 2 | N | —CH=CH— (E) | 21 | 195–196 | ethyl acetate |
| 4 | 2-Cl-phenyl-C(=N-)-O-C(CH₃)= | 2 | CH | —CH₂CH₂— | 43 | 124–125 | dichloromethane-ethyl acetate |
| 5 | cyclohexyl-C(=N-)-O-C(CH₃)= | 2 | CH | —CH₂CH₂— | 81 | 80–81 | dichloromethane-isopropyl ether |
| 6 | phenyl-C(=N-)-O-C(CH₃)= | 2 | CH | —CH₂— | 56 | 173–174 | methanol |
| 7 | phenyl-C(=N-)-O-C(CH₃)= | 2 | CH | —CH₂CH₂CH₂— | 56 | 124–125 | ethyl acetate-hexane |
| 8 | 2-thienyl-C(=N-)-O-C(CH₃)= | 2 | CH | —CH₂CH₂— | 47 | 143–144 | methanol |
| 9 | 3-CH₃-phenyl-C(=N-)-O-C(CH₃)= | 2 | CH | —CH₂CH₂— | 89 | 141–142 | dichloromethane-ethyl acetate |
| 10 | phenyl-N(CH₃)-C(=N-)-S-C(CH₃)= | 1 | CH | —CH₂CH₂— | 45 | 140–141 | methanol-ethyl acetate |

TABLE 5

A—(CH$_2$)$_n$—O—[phenyl(X,Y)]—CH(tetrazole)

| Example No. | A | n | X | Y | Yield (%) | Melting point (°C.) | Recrystallization Solvent |
|---|---|---|---|---|---|---|---|
| 11 | 2,4-dimethyloxazol-5-yl (CH$_3$, CH$_3$) | 2 | CH | —CH$_2$CH$_2$— | 45 | Note 1) 225–226 | methanol-ether |
| 12 | 5-methyl-2-phenyloxazol-4-yl | 1 | CH | (E) —CH=CH— | 85 | 214–215 | methanol-chloroform |
| 13 | 5-methyl-2-phenyloxazol-4-yl | 1 | CH | (E)—CH=CH (E)—CH=CH— | 57 | 203–204 | methanol |
| 14 | 5-methyl-2-phenyloxazol-4-yl | 1 | CH | —CH$_2$CH$_2$CH$_2$— | 25 | 107–108 | ethyl acetate-hexane |

[1)]sodium salt
Elemental analysis: calculated for C$_{16}$H$_{18}$N$_5$O$_2$Na.½H$_2$O
C, 55.81; H, 5.56; N, 20.34
Found C, 56.01; H, 5.82; N, 20.68

EXAMPLE 15

A mixture of (E)-5-[4-[4-(5-methyl-2-phenyl-4-oxazolylmethoxy)styryl]tetrazole (1.0 g), palladium-carbon (5%, 0.5 g) and dioxane (100 ml) was subjected to catalytic hydrogenation at room temperature. The catalyst was filtered off, and the filtrate was concentrated under reduced pressure to give 5-[2-[4-(5-methyl-2-phenyl-4-oxazolylmethoxy)phenyl]ethyl]tetrazole (0.81 g, 81%), which was recrystallized from methanol-chloroform to yield colorless plates, m.p.203°–204° C.

EXAMPLE 16

In substantially the same manner as in Example 15, 5-[4-[4-(5-methyl-2-phenyl-4-oxazolylmethoxy)phenyl]-1,3-butadien-1-yl]tetrazole was subjected to catalytic hydrogenation to yield 5-[4-[4-(5-methyl-2-phenyl-4-oxazolylmethoxy)phenyl]butyl]tetrazole, which was recrystallized from ethyl acetate—hexane to give colorless prisms, m.p.116°–117° C.

EXAMPLES 17–27

By a similar manner to Example 1, compounds shown in Table 6 and Table 7 were obtained.

TABLE 6

$$A-(CH_2)_n-O-\underset{\underset{Y}{|}}{C}H-\text{(tetrazole ring)}$$

| Example No. | A | n | Y | Melting point (°C.) | Yield (%) | Recrystallization Solvent |
|---|---|---|---|---|---|---|
| 17 | 2-phenyl-5-methyl-oxazol-4-yl | 1 | —C(CH$_3$)=CH—CH=CH— (E)(E) | 200–201 | 28 | chloroform-methanol-ether |
| 18 | 2-phenyl-5-methyl-oxazol-4-yl | 1 | —(CH$_2$)$_5$— | 129–130 | 46 | ethyl acetate-hexane |
| 19 | 4-phenyl-2,5-dimethyl-thiazol-... | 1 | —CH=CH—CH=CH— (E)(E) | 226–227 | 33 | chloroform-methanol |
| 20 | 4-phenyl-2,5-dimethyl-oxazol-... | 1 | —(CH$_2$)$_4$— | 126–127 | 13 | chloroform-isopropyl ether |
| 21 | 2-(2-naphthyl)-5-methyl-oxazol-4-yl | 1 | —CH=CH—CH=CH— (E)(E) | 162–163 | 20 | chloroform-methanol |

TABLE 7

| Example No. | A | n | Y | Melting point (°C.) | Yield (%) | Recrystallization Solvent |
|---|---|---|---|---|---|---|
| 22 | 2-(2-naphthyl)-5-methyl-oxazol-4-yl | 1 | —(CH$_2$)$_3$— | 156–157 | 29 | dichloromethane-ether |
| 23 | 2-(2-naphthyl)-5-methyl-oxazol-4-yl | 1 | —(CH$_2$)$_5$— | 139–140 | 23 | chloroform-ether |

TABLE 7-continued

| Example No. | A | n | Y | Melting point (°C.) | Yield (%) | Recrystallization Solvent |
|---|---|---|---|---|---|---|
| 24 | [phenyl-oxazole with CH₃, N, O] | 3 | (E) —CH=CH— | 185–186 | 40 | chloroform-methanol |
| 25 | [benzofuran-oxazole with CH₃] | 1 | —(CH₂)₃— | 121–122 | 46 | dichloromethane-isopropyl ether |
| 26 | [furan-oxazole with CH₃] | 1 | —(CH₂)₃— | 133–134 | 44 | dichloromethane-isopropyl ether |
| 27 | [phenyl-pyrazole with N-CH₃] | 1 | —(CH₂)₃— | 159–160 | 83 | dichloromethane-methanol |

EXAMPLE 28

According to the method described for Example 1, (E,E)-5-[3-(5-methyl-2-phenyl-4-oxazolylmethoxy)phenyl]-2,4-pentadienenitrile was allowed to react with sodium azide-ammonium chloride to give 5-[4-[3-(5-methyl-2-phenyl-4-oxazolylmethoxy)phenyl]-1,3-butadien-1-yl]tetrazole. Recrystallization from methanol gave colorless prisms, m.p.201°–202° C.

EXAMPLE 29

According to the method described for Example 1, (E,E)-5-[2-(5-methyl-2-phenyl-4-oxazolylmethoxy)phenyl]-2,4-pentadienenitrile was allowed to react with sodium azide-ammonium chloride to give 5-[4-[2-(5-methyl-2-phenyl-4-oxazolylmethoxy)phenyl]-1,3-butadien-1-yl]tetrazole. Recrystallization from dichloromethane-methanol gave colorless prisms, m.p.192°–193° C.

EXAMPLE 30 TO EXAMPLE 35

According to the method described Example 15, compounds set forth in [Table 8] were produced.

TABLE 8

| Example No. | | Melting point (°C.) | Yield (%) | Recrystallization Solvent |
|---|---|---|---|---|
| 30 | [structure: phenyl-oxazole-CH₂O-phenyl-(CH₂)₃-CH-tetrazole] | 94–95 | 81 | ethyl acetate-hexane |
| 31 | [structure: phenyl-oxazole-CH₂O-phenyl(CH₃)-(CH₂)₃-CH-tetrazole] | —¹⁾ | 41 | — |

TABLE 8-continued

| Example No. | Structure | Melting point (°C.) | Yield (%) | Recrystallization Solvent |
|---|---|---|---|---|
| 32 | | 126–127 | 43 | ethyl acetate-ether |
| 33 | | 162–164 | 62 | ethyl acetate-ether |
| 34 | | 148–149 | 55 | dichloromethane-methanol |
| 35 | | 112–113 | 14 | chloroform-ether |

EXAMPLE 36

In substantially the same manner as in Example 1, 5-[3-[2-(5-methyl-2-phenyl-4-oxazolylmethoxy)-5-pyridyl]propyl]-1H-tetrazole was obtained by reacting 4-[2-(5-methyl-2-phenyl-4-oxazolylmethoxy)-5-pyridyl]butyronitrile with sodium azide-ammonium chloride. The yield was 45%. Recrystallization from methanol-ethyl acetate gave colorless prisms, m.p. 137°–138° C.

EXAMPLE 37

In substantially the same manner as in Example 1, 5-[4-[2-(5-methyl-2-phenyl-4-oxazolylmethoxy)-5-pyridyl]butyl]-1H-tetrazole was obtained by reacting 5[2-(5-methyl-2-phenyl-4-oxazolylmethoxy)-5-pyridyl]valeronitrile with sodium azide-ammonium chloride. The yield was 46%. Recrystallization from ethyl acetate-hexane gave colorless prisms, m.p. 104°–105° C.

Formulation Example 1 (Preparation of tablets)

| | |
|---|---|
| (1) 5-[2-[4-[2-(5-methyl-2-phenyl-4-oxazolyl)-ethoxy]phenyl]ethyl]tetrazole (Compound produced in Example 1) | 10 g |
| (2) lactose | 50 g |
| (3) corn starch | 15 g |
| (4) carboxymethyl cellulose calcium | 44 g |
| (5) magnesium stearate | 1 g |
| 1000 tablets | 120 g |

The whole amounts of above (1), (2) and (3), and 30 g of (4) were kneaded with water, which was subjected to vacuum drying, followed by granulation. Thus-granulated powder was mixed with 14 g of (4) and 1 g of (5), followed by tableting using a tableting machine to prepare 1000 tablets containing 10 mg of (1) per tablet.

Formulation Example 2 (Preparation of tablets)

| | |
|---|---|
| (1) 5-[3-[4-[2-(5-methyl-2-phenyl-4-oxazolyl)-ethoxy]phenyl]propyl]tetrazole (Compound produced in Example 7) | 30 g |
| (2) lactose | 50 g |
| (3) corn starch | 15 g |
| (4) carboxymethyl cellulose calcium | 44 g |
| (5) magnesium stearate | 1 g |
| 1000 tablets | 140 g |

The whole amounts of above (1), (2) and (3), and 30 g of (4) were kneaded with water, which was subjected to vacuum drying, followed by granulation. Thus-granulated powder was mixed with 14 g of (4) and 1 g of (5), which was tableted by using a tableting machine to prepare 1000 tablets containing 30 mg of (1) per tablet.

We claim:

1. A compound of the formula

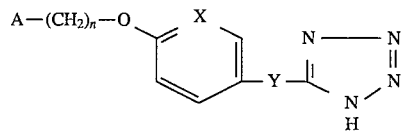

wherein n is an integer of 1 to 3,

A is an aromatic 5-membered cyclic residue of the formula

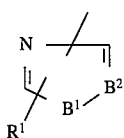

wherein
B¹ is a sulfur atom, oxygen atom, or NR group wherein
R is hydrogen a lower alkyl group having 1 to 3 carbon atoms, benzyl
or phenylethyl,
B² is N or C—R²
wherein
R² is hydrogen
or
a lower alkyl group which is unsubstituted or is substituted with hydroxyl group
R¹ is
(1) hydrogen,
(2) a hydrocarbon residue selected from the group consisting of
saturated aliphatic hydrocarbon residue having 1 to 8 carbon atoms,
unsaturated aliphatic hydrocarbon residue having 2 to 8 carbon atoms,
saturated alicyclic hydrocarbon residue having 3 to 7 carbon atoms,
unsaturated alicyclic hydrocarbon residue having 5 to 7 carbon atoms,
alicyclic-aliphatic hydrocarbon residue formed by bondage of the above-mentioned saturated or unsaturated alicyclic hydrocarbon residues and aliphatic hydrocarbon residues, and having 4 to 9 carbon atoms,
phenyl alkyl having 7 to 9 carbon atoms, naphthyl alkyl having 11 to 13 carbon atoms, phenyl, and naphthyl
(3) 5- or 6-membered heterocyclic ring selected from the group consisting of thienyl, furyl, pyridyl, thiazolyl, oxazolyl, imidazolyl, pyrimidinyl, pyrazinyl, pyridazinyl, piperidinyl, pyrrolidinyl, morpholinyl and tetrahydrofuryl, the 5- or 6- membered heterocyclic ring being bonded through a carbon atom, or
(4) amino group selected from the group consisting of
 a. N-monosubstituted amino group substituted by a lower alkyl having 1 to 4 carbon atoms, cycloalkyl having 3 to 7 carbon atoms, phenyl, naphthyl, pyridyl, thienyl, furyl, oxazolyl, thiazolyl, piperidinyl, pyrrolidinyl, morpholinyl, benzyl, phenethyl, acetyl, propionyl, carbamoyl group, N-monosubstituted carbamoyl group selected from the group consisting of
N-methylcarbamoyl, N-ethylcarbamoyl and N-propylcarbamoyl,
N,N-disubstituted carbamoyl group selected from the group consisting of
N,N-dimethylcarbamoyl, N-methyl-N-ethyl-carbamoyl and N,N-diethylcarbamoyl,
a lower alkoxycarbonyl group having 2 to 5 carbon atoms, hydroxyl group, a lower alkoxy group having 1 to 4 carbon atoms, benzyloxy, phenethyloxy and naphthyloxy,
 b. N,N-disubstituted amino group substituted by a substituent selected from substantially the same ones as in the above-mentioned N-monosubstituted amino group and by a substituent selected from the group consisting of alkyl group, cycloalkyl group, aryl group, aralkyl group,
and
 c. cyclic amino group selected from the group consisting of 1-azetidinyl, 1-pyrrolidino, piperidino, morpholino, piperazino, piperazino having, at the 4-position, lower alkyl having 1 to 4 carbon atoms, benzyl, phenethyl, naphthylmethyl, phenyl and naphthyl,
when the hydrocarbon residue contains an alicyclic group or when the 5- or 6-membered heterocyclic ring is a saturated one,
each of them may be substituted by one to three lower alkyl groups having 1 to 3 carbon atoms,
when the hydrocarbon residue contains an aromatic hydrocarbon residue or
when the 5- or 6- membered heterocyclic group is an unsaturated one,
it may have 1 to 4 substituents selected from the group consisting of halogen, hydroxyl, cyano, nitro, trifluoromethyl,
a lower alkoxy group having 1 to 4 carbon atoms,
a lower alkyl group having 1 to 4 carbon atoms,
a lower alkoxycarbonyl group having 2 to 4 carbon atoms,
a lower alkylthio having 1 to 3 carbon atoms, and
a lower alkyl amino having 1 to 4 carbon atoms,
R¹ and R² may be combined with each other to form a condensed ring if R¹ is combined with one of the ring-constituting carbon atoms adjacent to the carbon atom on which R² is substituted,
Y is a straight- or branched-chain divalent hydrocarbon residue selected from the group consisting of alkylene and alkenylene, and
X is CH or N,
or a pharmaceutically acceptable salt thereof.

2. A compound or pharmaceutically acceptable salt thereof according to claim 1, wherein
R¹ is hydrogen, hydrocarbon residue selected from the group consisting of
saturated aliphatic hydrocarbon residue having 1 to 8 carbon atoms,
unsaturated aliphatic hydrocarbon residue having 2 to 8 carbon atoms,
saturated alicyclic hydrocarbon residue having 3 to 7 carbon atoms,
unsaturated alicyclic hydrocarbon residue having 5 to 7 carbon atoms,
alicyclic-aliphatic hydrocarbon residue formed by bondage of the above-mentioned saturated or unsaturated alicyclic hydrocarbon residue and aliphatic hydrocarbon residues, and having 4 to 9 carbon atoms,
phenyl alkyl having 7 to 9 carbon atoms, naphthyl alkyl having 11 to 13 carbon atoms, phenyl
and naphthyl
or
5- or 6-membered heterocyclic ring selected from the group consisting of thienyl, furyl, pyridyl, thiazolyl, oxazolyl, imidazolyl, pyrimidinyl, pyrazinyl, pyridazinyl, piperidinyl, pyrrolidinyl, morpholinyl and tetrahydrofuryl, the 5- or 6- membered heterocyclic ring being ring being bonded through a carbon atom, and when the hydrocarbon or 5- or 6-membered heterocyclic ring contains an alicyclic group or when the 5- or 6heterocyclic ring is a saturated one, each of them may be substituted by one to three lower alkyl groups having 1 to 3 carbon atoms, and when the hydrocarbon residue contains an aromatic hydrocarbon residue or when the 5- or 6-membered heterocyclic ring is an unsaturated one, it may have 1 to 4 substituents selected from the group consisting of halogen, hydroxyl, cyano, nitro, trifluoromethyl, a lower alkoxy group having 1 to 4 carbon, atoms, a lower alkyl group having 1 to 4 carbon atoms, a lower alkoxycarbonyl group having 2 to 4 carbon atoms, a lower alkylthio having 1 to 3 carbon atoms, and a lower alkyl amino having 1 to 4 carbon atoms, and $R^1$ and $R^2$ may be combined with each other to form a condensed ring if $R^1$ is combined with one of ring-constituting carbon atoms adjacent to the carbon atom on which $R^2$ is substituted.

3. A compound as claimed in claim 2, wherein $B^1$ is S, O or NR (wherein R is hydrogen, a lower alkyl group or an aralkyl group), and $B^2$ is N, or a pharmaceutically acceptable salt thereof.

4. A compound as claimed in claim 1, wherein n is 1 or 2, or a pharmaceutically acceptable salt thereof.

5. A compound as claimed in claim 1, wherein X is CH, or a pharmaceutically acceptable salt thereof.

6. A compound as claimed in claim 1, wherein Y contains 1 to 5 carbon atoms, or a pharmaceutically acceptable salt thereof.

7. A compound as claimed in claim 1, wherein Y is an alkylene having 1 to 5 carbon atoms, or a pharmaceutically acceptable salt thereof.

8. A compound as claimed in claim 1, wherein Y is —CH$_2$CH$_2$CH$_2$— or —CH$_2$CH$_2$CH$_2$CH$_2$—, or a pharmaceutically acceptable salt thereof.

9. A compound as claimed in claim 1, wherein the compound is 5-[2-[4-[2-(5-methyl-2-phenyl-4-oxazolyl)ethoxy]phenyl]ethyl]tetrazole or a pharmaceutically acceptable salt thereof.

10. A compound as claimed in claim 1, wherein the compound is 5-[2-[2-[2-(5-methyl-2-phenyl-4-oxazolyl)ethoxy]-5-pyridyl]ethyl]tetrazole or a pharmaceutically acceptable salt thereof.

11. A compound as claimed in claim 1, wherein the compound is 5-[3-[4-(5-methyl-2-phenyl-4-oxazolylmethoxy)phenyl]propyl]tetrazole or a pharmaceutically acceptable salt thereof.

12. A compound as claimed in claim 1, wherein the compound is 5-[4-[4-(5-methyl-2-phenyl-4-oxazolylmethoxy)phenyl]butyl]tetrazole or a pharmaceutically acceptable salt thereof.

13. A compound as claimed in claim 1, wherein the compound is 5-[5-[4-(5-methyl-2-phenyl-4-oxazolylmethoxy)phenyl]pentyl]tetrazole or a pharmaceutically acceptable salt thereof.

14. A compound as claimed in claim 1, wherein the compound is 5-[3-[4-[5-methyl-2-(2-naphthyl)-4-oxazolylmethoxy]phenyl]propyl]tetrazole or a pharmaceutically acceptable salt thereof.

15. A compound as claimed in claim 1, wherein the compound is 5-[5-[4-[5-methyl-2-(2-naphthyl)-4-oxazolylmethoxy]phenyl]pentyl]tetrazole or a pharmaceutically acceptable salt thereof.

16. A compound as claimed in claim 1, wherein the compound is 5-[3-[4-[5-methyl-2-(2-furyl)-4-oxazolylmethoxy]phenyl]propyl]tetrazole or a pharmaceutically acceptable salt thereof.

17. A compound as claimed in claim 1, wherein the compound is 5-[3-[4-(1-methyl-5-phenyl-1,2,4-triazol-3-ylmethoxy)phenyl]propyl]tetrazole or a pharmaceutically acceptable salt thereof.

18. A compound as claimed in claim 1, wherein the compound is 5-[3-[4-[5-methyl-2-(benzo[b]furan-2-yl)-4-oxazolylmethoxy]phenyl]propyl]tetrazole or a pharmaceutically acceptable salt thereof.

19. A compound of the formula

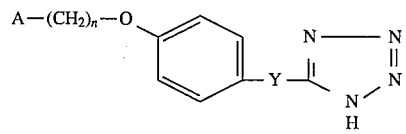

wherein n is an integer of 1 to 3,

A is

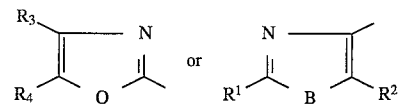

wherein

B is O or S, $R^1$ is hydrogen, saturated aliphatic hydrocarbon of 1–8 carbon atoms, phenyl alkyl of 7 to 9 carbon atoms, naphthyl alkyl of 11 to 13 carbon atoms, phenyl or naphthyl, $R^2$ is hydrogen, a lower alkyl group, or a hydroxy lower alkyl group, each of $R^3$ and $R^4$ is independently hydrogen, saturated aliphatic hydrocarbon of 1 to 8 carbon atoms, phenyl alkyl of 7 to 9 carbon atoms, naphthyl alkyl of 11 to 13 carbon atoms, phenyl or naphthyl, and Y is alkylene of 1 to 5 carbon atoms, or a pharmaceutically acceptable salt thereof.

20. A therapeutic composition for the treatment of diabetes which comprises an effective amount of a compound or pharmaceutically acceptable salt as defined in claim 1 and a pharmaceutically acceptable carrier therefore.

21. A therapeutic composition for the treatment of hyperlipemia which comprises an effective amount of a compound or pharmaceutically acceptable salt as defined in claim 1 and a pharmaceutically acceptable carrier therefore.

22. A method for the treatment of a patient suffering from diabetes, which comprises administering to such patient an effective amount of a compound or pharmaceutically acceptable salt as defined in claim 1.

23. A method for the treatment of a patient suffering from hyperlipemia, which comprises administering to such patient an effective amount of a compound or pharmaceutically acceptable salt as defined in claim 1.

24. A compound or pharmaceutically acceptable salt according to claim 1 wherein A is a group of the formula

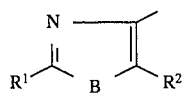

wherein
- $R^1$ is hydrogen, hydrocarbon residue selected from the group consisting of
  - saturated aliphatic hydrocarbon residue having 1 to 8 carbon atoms,
  - unsaturated aliphatic hydrocarbon residue having 2 to 8 carbon atoms,
  - saturated alicyclic hydrocarbon residue having 3 to 7 carbon atoms,
  - unsaturated alicyclic hydrocarbon residue having 5 to 7 carbon atoms,
  - alicyclic-aliphatic hydrocarbon residue formed by bondage of the above-mentioned saturated or unsaturated alicyclic hydrocarbon residue and aliphatic hydrocarbon residues, and having 4 to 9 carbon atoms,
  - phenyl alkyl having 7 to 9 carbon atoms, naphthyl alkyl having 11 to 13 carbon atoms, phenyl and
  - naphthyl or
- 5- or 6-membered heterocyclic ring selected from the group consisting of thienyl, furyl, pyridyl, thiazolyl, oxazolyl, imidazolyl, pyrimidinyl, pyrazinyl, pyridazinyl, piperidinyl, pyrrolidinyl, morpholinyl and tetrahydrofuryl, the 5- or 6- membered heterocyclic ring being bonded through a carbon atom,
  - when the hydrocarbon or 5- or 6-membered heterocyclic ring contains an alicyclic group or
  - when the 5- or 6-membered heterocyclic ring is a saturated one,
    - each of them may be substituted by one to three lower alkyl groups having 1 to 3 carbon atoms, and
  - when the hydrocarbon residue contains an aromatic hydrocarbon residue or
  - when the 5- or 6-membered heterocyclic ring is an unsaturated one,
    - it may have 1 to 4 substituents selected from the group consisting of
      - halogen, hydroxy, cyano, nitro, trifluoromethyl,
      - a lower alkoxy group having 1 to 4 carbon atoms,
      - a lower alkyl group having 1 to 4 carbon atoms,
      - a lower alkoxycarbonyl group having 2 to 4 carbon atoms,
      - a lower alkylthio having 1 to 3 carbon atoms, and
      - a lower alkyl amino having 1 to 4 carbon atoms,
  - $R^2$ is hydrogen or
  - a lower alkyl group optionally substituted with hydroxyl group;

and
  - B is O or
  - S.

25. A compound or pharmaceutically acceptable salt according to claim 1 wherein A is a group of the formula

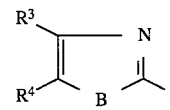

wherein
  - B is O or
  - S,
  - each of $R^3$ and $R^4$ is hydrogen,
    - hydrocarbon residue selected from the group consisting of saturated aliphatic hydrocarbon residue having 1 to 8 carbon atoms,
    - unsaturated aliphatic hydrocarbon residue having 2 to 8 carbon atoms,
    - saturated alicyclic hydrocarbon residue having 3 to 7 carbon atoms,
    - unsaturated alicyclic hydrocarbon residue having 5 to 7 carbon atoms,
    - alicyclic-aliphatic hydrocarbon residue formed by bondage of the above-mentioned saturated or unsaturated alicyclic hydrocarbon residue and aliphatic hydrocarbon residues, and having 4 to 9 carbon atoms,
    - phenyl alkyl having 7 to 9 carbon atoms,
    - naphthyl alkyl having 11 to 13 carbon atoms,
    - phenyl and
    - naphthyl or
  - 5- or 6-membered heterocyclic ring selected from the group consisting of thienyl, furyl, pyridyl, thiazolyl, oxazolyl, imidazolyl, pyrimidinyl, pyrazinyl, pyridazinyl, piperidinyl, pyrrolidinyl, morpholinyl and tetrahydrofuryl, the 5- or 6- membered heterocyclic ring being bonded through a carbon atom,
    - when the hydrocarbon or 5- or 6- membered hetero-cyclic ring contains an alicyclic group or
    - when the 5- or 6- membered heterocyclic ring is a saturated one,
      - each of them may be substituted by one to three lower alkyl groups having 1 to 3 carbon atoms, and
      - when the hydrocarbon residue contains an aromatic hydrocarbon residue or
      - when the 5- or 6- membered heterocyclic ring is an unsaturated one,
        - it may have 1 to 4 substituents selected from the group consisting of halogen, hydroxyl, cyano, nitro, trifluoromethyl,
        - a lower alkoxy group having 1 to 4 carbon atoms,
        - a lower alkyl group having 1 to 4 carbon atoms,
        - a lower alkoxycarbonyl group having 2 to 4 carbon atoms,
        - a lower alkylthio having 1 to 3 carbon atoms, and
        - a lower alkyl amino having 1 to 4 carbon atoms,
or they may be combined with each other to form a condensed ring.

26. A method of producing a compound of the formula:
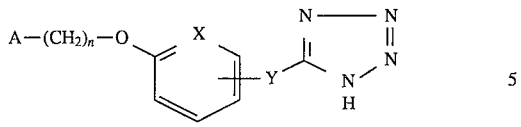
wherein n is an integer of 1 to 3; A is an optionally substituted heterocyclic residue; Y is a divalent hydrocarbon residue; and X is for CH or N, which comprised allowing a compound of the formula:
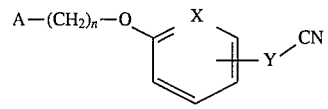
wherein each symbol is of the same meaning as defined above to react with a metal azide compound.
* * * * *